Figure 1:
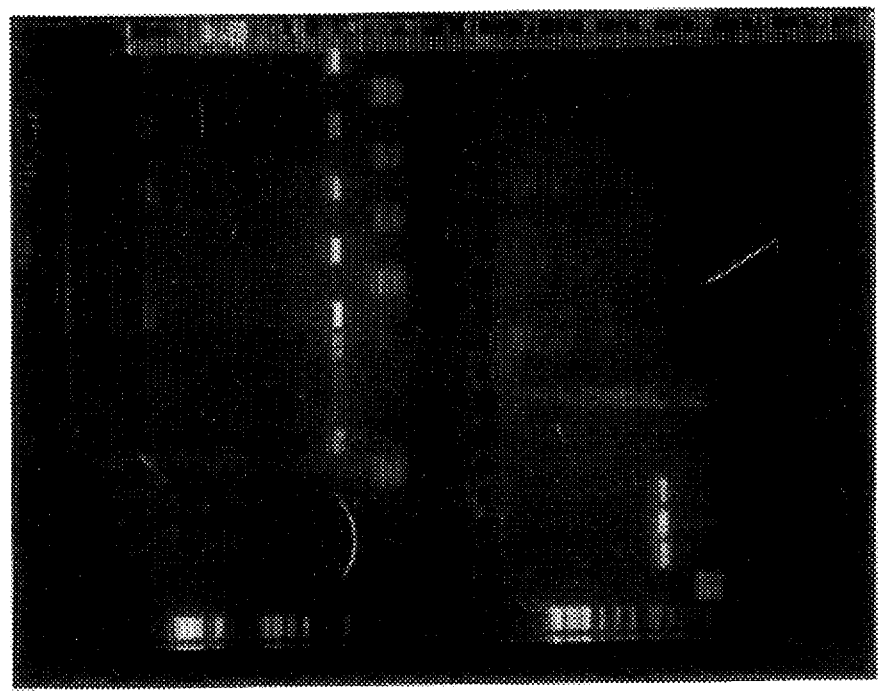

US005767265A

United States Patent [19]

Eberle et al.

[11] Patent Number: 5,767,265
[45] Date of Patent: Jun. 16, 1998

[54] MONKEY HERPES B VIRUS GENES

[75] Inventors: Richard Eberle; Darla Black, both of Stillwater, Okla.; Franco Scinicariello; Julia Hilliard, both of San Antonio, Tex.

[73] Assignee: Southwest Foundation for Biomedical Research, San Antonio, Tex.

[21] Appl. No.: 541,878

[22] Filed: Oct. 10, 1995

Related U.S. Application Data

[62] Division of Ser. No. 42,747, Apr. 1, 1993, Pat. No. 5,487,969.

[51] Int. Cl.$^6$ .............................. C07H 21/04; C12N 15/11
[52] U.S. Cl. ........................... 536/24.32; 435/5; 530/350; 530/395
[58] Field of Search .......................... 435/5; 536/24.32; 530/350, 395

[56] References Cited

PUBLICATIONS

Wall, et al., Discrimination Between Twenty Isolates of Herpesvirus Simiae (B virus) by Restriction Enzyme Analysis of the Viral Genome, Virus Research, 12, pp. 283–296 (1989).
Sabin, et al., Acute Ascending Myelitis Following a Monkey Bite, With The Isolation of a Virus Capable of Reproducing the Disease, Journal of Experimental Med., vol. 59, pp. 115–136 (1934).
Ou, et al., DNA Amplification for Direct Detection of HIV-1 in DNA of Peripheral Blood Mono–nuclear Cells, Science, Col. 239, pp. 295–297 (1987).
Saike, et al., Enzymatic Amplification of B–Globin Genomic Sequences and Restriction Site Analysis of Diagnosis of Sickle Cell Anemia, Science, vol. 230, pp. 1350–1354 (1985).
McCarthy, et al., A Review of Primate Herpes Viruses, Proc. Roy Soc., Med., vol. 68, pp. 145–150 (1975).
Fitzpatrick, et al., Mapping of 10 Epitopes on Bovien Herpesvirus Type 1 Glycoproteins gI and gIII Virology, 176, pp. 145–157 (1990).
Bzik, et al., Nucleotide Sequence Specifying the Glycoprotein Gene, gB, of Herpes Simplex Virus Type 1, Virology, 133, pp. 301–314 (1984).
Pierce, et al., B Virus, Its Current Significance, Am. J. Hyc., vol. 58, pp. 242–250 (1958).
Davidson, et al., B Virus Infection in Man, Ann. NY Acad. Sci., vol. 85, pp. 970–979 (1960).
Kebble, B Virus Infection in Monkeys, Ann. NY Acad. Sci., vol. 85, pp. 960–969 (1960).
Hilliard, et al., Herpesvirus Simiae (B Virus); Replication of the Virus and Identification of Viral Polypeptides in Infected Cells, Archives of Virology, 93, pp. 185–198 (1987).
Hilliard, et al. Simian Alphaherpesviruses and Their Relation to the Human Herpes Simplex Viruses, Archives of Virology, 109, pp. 83–102 (1989).

Eberle, et al., Relaedness of Glycoproteins Expressed on the Surface of Simian Herpes–Virus Virions and Infected Cells to Specific HSV Glycoproteins, Archives of Vir., 109, pp. 233–252 (1989).
Borchers, et al. Convserved Epitopes of Simian Herpesvirus SA8 and Bovine Herpesvirus Type 2, Archives of Virology, 111, pp. 1–14 (1990).
Rodu, et al. Simplified PCR–Based Detection and Typing Strategy for Human Papillamaviruses Utilizing a Single Oligonucleotide Primer Set, Biotechniques, 10, pp. 632–636 (1991).
Vizoso, Recovery of Herpes Simiae (B Virus) From both Primary and Latent Infections in Rhesus Monkeys, Br. J. Exp. Path., 56, pp. 485–488 (1975).
Shibata, et al. Detection of Human Papilloma Virus in Paraffin–Embedded Tissure Using the Polmerase Chain Reaction, J. Exp. Med., Vo. 167, pp. 225–230 (1988).
Desroriers, et al., Herpesvirus Tamarinus and its Relation to Herpers Simplex Virus, J. Gen. Virol 56, pp. 119–130 (1981).
Chase, et al., The Effect of Bovine Herpesvirus Type 1 Glycoproteins gI and gIII on Herpesvirus infections, J. Gen. Virol., 70 pp. 1561–1569 (1989).
Fujinaga, et al., Simultaneous Detection and Typing of Genital Human Papillamavirus DNA using the Polymerase Chain Reaction, Journal of General Virology, 72, pp. 1039–1044 (1991).
Nagler, et al., A Fatal B. Virus Infection in a Person Subject to Recurrent Herpes Labialis, Canad M.A.J., Vo. 79, pp. 743–745 (1958).
Barahona, et al., A Compendium Of Herpesviruses Isolated from NonHuman Primates, Intervirology, 3, pp. 175–192 (1974).
Boulter, The Isolation of Monkey B Virus ( Herpesvirus Simiae) from the Trigeminal Gaglia of a Healthy Seropositive Rhesus Monkey, Journal of Biological Standardization, 2, pp. 279–280.
Gary, et al., Comparative Complement Fixation and Serum Neutralization Antibody Titers to Herpes Simplex Virus Tyope 1 and Herpesvirus Simiae in Macaca Mulatta and Humans, Journal of Clinical Microbiology, vol. 5, No. 4, pp. 465–470 (1977).
Palmer, B Virus Herpesvirus Simiae: Historical Perspective., J. Med. Primatol. 16, pp. 99–130 (1987).

(List continued on next page.)

*Primary Examiner*—Scott W. Houtteman
*Attorney, Agent, or Firm*—Cox & Smith Incorporated

[57] ABSTRACT

With the DNA sequence (SEQ ID NO:4:) of monkey B virus which codes for the gB glycoprotein (UL27) (SEQ ID NO:6:) and a portion (UL28) (SEQ ID NO:5:) of an ICP 18.5 kilodalton polypeptide (UL28), methods for early detection of the presence of monkey B virus in humans and monkeys can be performed by amplifying primer sequences and distinguishing the monkey B virus DNA coding for UL27 or UL28 from other herpes virus gB DNA using unique reaction conditions to permit unequivocal differentiation.

3 Claims, 2 Drawing Sheets

OTHER PUBLICATIONS

Dalgard, Herpesvirus Simiae Claims the Life of Primate Veterinarian, J. Med. Primatol, vol. 20 (1991).

Katz, et al., ELISA for Detection of Group–Common and Virus–Specific Antibodies in Human and and Simian Sera Induced by Herpes Simplex and Related Simian Viruses, Journal of Virology Methods 14, pp. 99–109 (1986).

Hilliard, et al., Rapid Identification of Herpesvirus Simiae (B Virus) DNA from Clinical Isolates in Non–Human Primate Colonies, Journal of Virological Methods, 13, pp. 55–62 (1986).

Eberle, et al. Replication of Simian Herpesvirus SA8 and Identification of Viral Polypeptides in Infected Cells, Journal of Virology, vol. 50, pp. 316–324 (1984).

Pellett, et al. Anatomy of the Herpes Simplex Virus 1 Strain F Glycoprotein B Gene: Primary Sequence and Predicted Protein Structure of the Wild Type and of Monoclonal Antibody–Resistance Mutants, Juournal of Virology, Vo. 53, pp. 243–253 (1985).

Stuve, et al. Structure and Expression of the Herpes Simplex Virus Type 2, Journal of Virology, vol. 61, pp. 326–335 (1987).

Drunken Littel, et al., Synthesis, Cellular Location, and Immunogencity of Bovine Herpesvirus 1 Glycoproteins gI and gIII Expressed by Recombiant Vaccinia Virus, Journal of Virology, vol. 63, pp. 2159–2168 (1989).

Horbal, et al. Continuous Epitopes of the Human Immunodeficiency Virus Type 1 (HIV–1) Transmembrane Glycoprotein and Reactivity of Human Sera to Synthetic Peptides Representing Various HIV–1 Isolate Journal of Virology, vol. 65, pp. 2718–2723 (1991).

Powdrill, et al. Immunologic Priming with Recombinant Hepatitis A Virus Capside Proteins Produced In *Esherichia coli*, Journal of Virology, vol. 65, pp. 2686–2690 (1991).

Huang, et al. Localization of Immunogenic Domains in the Human Immunodeficiency Virus Type 2 Envelope, Journal of Virology, vol. 65, pp. 5073–5079 (1991).

Herberling, et al., A Dot–Immunobinding Assay on Nitrocellulose with Psoralen Inactive Herpesvirus simiae, Laboratory Animal Science, Vo. 77, pp. 304–308 (1987).

Boulter, et al., A Comparison of Neutralization Tests for the Detection of Antibodies to Herpes–virus simiae (monkey B Virus), Labatory Animal Science, pp. 150–152 (1982).

Zwartouw, et al., Transmission of B Virus Infection Between Monkeys Especially in Relation to Breeding Colonies, Laboratory Animals, 18, pp. 125–130 (1984).

Zwartouw, et al., Escretion of B Virus in Monkeys and Evidence of Genital Infection, Laboratory Animals, 18, pp. 65–70 (1984).

Rowley, et al., Rapid Dtection of Herpes–Simplex–Virus DNA in Cerebrospinal Fluid in Patients with Herpes Simplex Encephalitis, The Lancelot, vol. 1, pp. 440–441 (1990).

Griffin, et al., B–Virus Infection in Humans—Pensacola, Florida, Epidemiologic Notes and Reports, vol. 35, No. 19, pp. 289–296 (1987).

Davenport, et al. B–VirusIinfections in Humans—Michigan, Epidemiologic Notes and Reports, vol. 38, pp. 453–454 (1989).

MONKEY HERPES B VIRUS GENES

This is a divisional of application Ser. No. 08/042,747 filed Apr. 1, 1993, now U.S. Pat. No. 5,487,969.

The work leading to the present invention was partially supported by National Institutes of Health Grants Nos. P40 RR05162 and 401 RR03163. The U.S. Government may hold rights in the present patent.

FIELD OF THE INVENTION

This invention relates to a DNA segment (SEQ ID NO:4:) or a unique portion thereof from the monkey B virus which codes for gB glycoprotein (UL27) (SEQ ID NO:6:) and a portion (SEQ ID NO:5:) of an ICP 18.5 kilodalton polypeptide (UL28). The invention further relates to the use of this DNA segment (SEQ ID NO:4:) in assays for detecting monkey B virus infection.

BACKGROUND OF THE INVENTION

At present, eight α-herpes viruses indigenous to primates are known. Several journal articles describing the Simian herpes viruses have been published (R. N. Hull, *The Simian Herpes Viruses* in The Herpes Viruses (D. S. Kaplan ed., *Academic Press,* 1973); K. McCarthy and F. A. Tosolini *Proc. Roy. Soc. Med.,* 68:11–16 (1975)). Early studies using virus neutralization assays (Hull (1973)) and more recent molecular studies have demonstrated (R. C. Desrosiers and L. A. Folk, *J. Gen. Virol*,. 56:119–130 (1981); R. Eberle and J. K. Hilliard, *J. Virol.,* 50:316–324 (1984); Mou et al, *Arch. Virol.* 91:117–133 (1986); R. Eberle et al, *Arch. Virol.,* 109:233–252 (1989); J. K. Hilliard et al, *Arch. Virol.,* 109:83–102 (1989); K. Borchers et al, *Arch. Virol.,* 111:1–14 (1990)) that six of these viruses are closely related to each other. These are the two human herpes simplex viruses, HSV1 and HSV2; a virus indigenous to African monkeys, SA8 (herpes virus cercopithecus); monkey B virus (herpes virus simiae), which is indigenous in Asiatic macaques; herpes virus saimri 1, which is indigenous in South American squirrel monkeys; and herpes virus ateles 1, which is indigenous in South American spider monkeys. In its natural host species, B virus causes self-limiting oral and genital lesions similar to those produced in humans by HSV1 and HSV2 (S. A. Keeble, *Ann. N. Y Acad. Sci.,* 85:9960–9969 (1960); H. T. Zwartouw and E. A. Boulter, *Lab. Anim.,* 18:65–70 (1984); H. T. Zwartouw et al, *Lab. Anim.,* 18:125–130 (1984)). Humans can contract B virus by bites or scratches inflicted by macaques (W. L. Davidson and K. Hummeler, *Ann. N.Y. Acad. Sci.,* 85:970–979 (1960). In humans, untreated B virus infections are severe and usually fatal (A. B. Sabin and A. M. Wright, *J. Exp. Med.,* 59:115–136 (1934); S. P. Nagler and M. Klotz, *Canad. Med. Assoc. J.,* 79:743–745 (1958); E. C. Pierce et al, *Am. J. Hyg.,* 68:242–250 (1958); Centers for Disease Control, *MMWR,* 36:289–296 (1987); S. S. Kalter and R. L. Heberling, *Lab. Anim.,* 18:31–34 (1989). In recent cases of human B virus infection, experimental drug therapy has been effective at preventing mortality. However, the experimental nature of these drugs and the duration over which they must be used necessitates definitive B virus diagnosis prior to their use. The severe nature of B virus infections in humans has resulted in attempts, both past and ongoing, to establish B virus-free colonies of macaques for research use. Identification of B virus infected monkeys is an integral part of establishing such colonies.

B virus is closely related to both the human HSVs and to SA8 (J. K. Hilliard et al, *Arch. Virol.,* 93:185–198 (1987); Hilliard et al (1989); Eberle et al, (1989)). Most humans have antibodies to HSV1 and/or HSV2, most adult macaques have antibodies to B virus, and most adult baboon have antibodies to SA8. Since antibodies to any one of these viruses will react with all four of these viruses, it is difficult to serologically diagnose the virus by which the antibodies were originally induced (i.e., the virus with which an individual is infected). Using sensitive and specialized assays, this can be done, albeit with considerable time, expertise, specialized biocontainment an expense (D. Katz et al, *J. Virol. Methods,* 14:99–109 (1986); R. Heberling and S. S. Kalter, *Lab. Anim. Sci.,* 37:304–308 (1987)). Similarly, currently employed techniques for identification of B virus or SA8 in clinical specimens requires not only the considerable time and expense associated with performing virus isolations but also additional testing to determine whether the virus isolated is HSV1, HSV2, B virus, or SA8 (R. Eberle and D. Black, *Arch. Virol.,* 118:67–86 (1991); J. K. Hilliard et al, *J. Virol Methods,* 13:55–62 (1986)). In addition, there are strict regulations regarding the biosafety containment facilities necessary to work with biological samples suspected or known to contain B virus. This currently limits diagnostic activities for B virus in the United States to two laboratories.

B virus (Herpesvirus simiae) infection is an occupational hazard for monkey handlers and those who come into contact with macaque mucosal secretions and/or tissues, e.g., kidney cells frequently used for primary cell culture. Although B virus infections in humans are not common, the increased usage of macaque monkeys in biomedical research, especially AIDS research, has been associated with an increased frequency of human exposure to B virus with four fatalities in the past five years (Centers for Disease Control, *MMWR.,* 36:289–296 (1987); Centers for Disease Control, *MMWR.,* 38:353–354 (1989); *J. Med. Primatol.,* 20:373 (1991)).

B virus, an α-herpes virus, is enzootic in rhesus (Macaca mulatta), cynomolgus (Macaca fascicularis) and other Asiatic monkeys of the genus Macaca (A. E. Palmer, *J. Med. Primatol.,* 16:99–130 (1987)). It was first isolated in 1934 from a fatal human case following a bite from an apparently normal rhesus monkey (Sabin and Wright, (1934)). B virus is morphologically, biologically, and antigenically similar to herpes simplex virus types 1 and 2 (HSV1 and HSV2). Like HSV1 and HSV2 infections in humans, primary infection with B virus in macaques can result in gingivostomatitis, conjunctivitis or genital infections (Zwartouw and Boulter (1984)). Nonlesional, asymptomatic disease can also occur. Following primary infection, B virus can establish latency in the host and can reactivate spontaneously or in response to stress, resulting in shedding of virus in saliva and/or genital secretions even in the absence of visible lesions (A. D. Vizoso, *Br. J. Exp. Pathol.,* 56:485–488 (1975); E. A. Boulter, *J. Biol. Stand.,* 3:279–280 (1975)). In humans, B virus infection contracted by accidental monkey bite or from infected tissues or body fluids causes acute ascending myelitis, which leads to death from respiratory paralysis (Palmer (1987)). The recent outbreaks of B virus infection in humans, resulting in four fatalities including the demonstration of the first human to human B virus transmission, underscores the importance of rapid diagnosis of infection (CDC (1987); CDC (1989)). Rapid identification of infection permits early antiviral intervention reducing morbidity and mortality.

Currently, the diagnosis of B virus infection is accomplished primarily by isolation and identification of the virus. However, this method of detection requires strict biosafety containment facilities and specialized personnel. Given the high survival-value of antiviral treatments sufficiently early in the course of the disease. a rapid. specific and sensitive diagnostic test is needed. Polymerase chain reaction (PCR) technique (R. K. Saiki et al. Science, 230:1350– 1354 (1985)). which allows the enzymatic amplification of minute quantities of DNA often undetectable by other methods. has been widely used for detection of several viral agents such as HSV (A. H. Rowley et al. Lancet. 335:440–441 (1990)). human immunodeficiency virus (HIV) (C-Y Ou et al. Science, 239:295–297 (1988)) and human papilloma viruses (HPV) (D. Shibata. J. Exp. Med., 167:225–230 (1988)). The applicants herein use PCR for detection of B virus in human and monkey samples.

Concern about the occupational health hazards associated with handling monkeys infected with B virus. as well as other zoonotic infections. has led to a recognized need for B virus-free breeding colonies. The increased usage of macaques in biomedical research underscores the importance for rapid diagnosis of B virus infections. The recent human fatalities might each have been avoided by early diagnosis. To date. laboratory diagnosis of B virus infection has been achieved primarily by virus culture. After virus isolation in suitable cell lines. the identification of the virus is accomplished either by neutralization assay (G. W. Gary and E. L. Palmer. J. Clin. Microbiol., 5:465–470 (1977)) or by molecular biology assays. Virus neutralization assays are cumbersome. time consuming and tedious. Furthermore. they often yield equivocal results. Using molecular biology assays. virus identification and differentiation can be performed by i) analysis of infected-cell polypeptides on SDS-polyacrylamide gels (Hlliard et al (1987)). or ii) restriction-endonuclease analysis of infected-cell DNA (Hilliard et al. J. Virol. Methods, 13:55–62 (1986); L. V. M. Wall et al. Virus Res., 12:283–296 (1989).

Such molecular biology assays for the purpose of diagnosis of monkey B virus infection can only be performed if the exact sequence of monkey B virus DNA and the proteins for which it codes are known and. furthermore. a method is devised for separating out and identifying the monkey B virus DNA and/or protein sequences from the infected cells. Before the present invention. the necessary sequence data and such a method for separating and identifying monkey B virus DNA from infected cells has not been known or obtainable.

SUMMARY OF THE INVENTION

The invention relates to a substantially pure form of a DNA segment (SEQ ID NO:4) of herpes simian monkey B virus coding for gB glycoprotein (UL27) (SEQ ID NO:6:) and a portion (SEQ ID NO:5:) of an ICP 18.5 kilodalton polypeptide (UL28), as well as some non-coding sequences. The invention further relates to a unique portion of this DNA segment.

The invention further relates to a protein (SEQ ID NO:6:) of gB glycoprotein (UL27) of herpes simian monkey B virus.

Additionally, the invention relates to a recombinant DNA molecule comprising a substantially pure DNA segment of herpes simian monkey B virus (SEQ ID NO:4:) and a vector for introducing the DNA segment into a host cell.

Furthermore, this invention relates to a method for detecting the presence of herpes simian monkey B virus in an individual comprising the steps of:

a) obtaining a tissue sample or a culture sample from an individual suspected of being infected with herpes simian monkey B virus;

b) extracting DNA from the tissue sample;

c) amplifying DNA segments from the extracted DNA, the DNA segments comprising at least a portion of a DNA segment (SEQ ID NO:4:) of herpes simian monkey B virus; and d) analyzing the amplified DNA segments to detect the presence of DNA sequences comprising at least a portion of the DNA segment (SEQ ID NO:4:).

Various other objects and advantages of the present invention will become apparent from the following figures and description of the invention.

BRIEF DESCRIPTION OF THE DRAWINGS

FIG. 1. Ethidium bromide-stained agarose gel analysis of undigested and SacII-cleaved (marked c) PCR products.

Lane 1 contains the internal controls to assure that no DNA transfer contamination occurred during the PCR procedure. Lane 2 contains amplified Vero cell DNA as a negative control. Lane 3 contains B-virus strain (E2490). Lane 4 contains HSV-2 strain (186). Lane 5 contains HSV-1 strain (KOS). Lanes 6–9 contain B virus isolates from one infected human and three infected monkeys, respectively. The M represents the marker DNAs, on the left the Hae III digested ϕX174 RF DNA and on the right the ϕX174 Hinf I markers. The arrows indicate the size in base pairs. Only the amplified DNA of B virus isolates yielded two subfragments after Sac II-cleavage.

FIG. 2. Southern blot of PCR products of human sample DNA hybridized with oligonucleotide probe.

Lanes 1 and 4 are negative controls. Lanes 2, 3, 5, 6 and 7 are patient samples. Lane 8 is a B virus control. Lane 9 is HSV-1 control. Lane 10 is HSV-2 control.

DETAILED DESCRIPTION OF THE INVENTION

The DNA segment (SEQ ID NO:4:) of monkey B virus coding for the gB glycoprotein (UL27) (SEQ ID NO:6:) and a portion (SEQ ID NO:5:) of an ICP 18.5 kilodalton polypeptide (UL28) described here has been used as a basis for the development of differential diagnostic tests for rapid testing of suspect B virus cases. Comparison of the B virus gB glycoprotein sequence with sequences of gB proteins of other primate α-herpes viruses allows identification of regions which are strongly conserved among all of the primate α-herpes viruses and other regions which are highly divergent among them (Eberle, unpublished results). These observations together with the DNA sequences of the B virus (SEQ ID NO:4:), SA8 (SEQ ID NO:7:), HSV1 and HSV2 gB genes have been used to develop synthetic DNA primers BV1 (SEQ ID NO:1:) and BV2 (SEQ ID NO:2:) which are homologues to sequences of conserved regions and which flank a divergent region of the gene. These primers can be used in polymerase chain reactions (PCR) to amplify the flanking divergent region from any primate α-herpes virus DNA present in clinical or laboratory specimens. Knowing the DNA sequence of the divergent region of each of the four virus genes, the amplified product can then be further analyzed by determination of its size, restriction enzyme digestion pattern, or its DNA sequence to determine which of the four viruses it is derived from and hence which virus is present in the clinical specimen. A similar approach has been used by other investigators for detection and differential identification of various serotypes of papilloma viruses (Y. Fujinaga et al, *J. Gen. Virol.*, 72:1039–1044 (1991); B. Rodu et al, *Biotechniques*, 10:632–637 (1991)) but has not been applied to differential diagnosis of primate herpes viruses. Cloned or PCR-generated sequences derived from divergent (virus-specific) regions of the B virus gB gene sequence can also be utilized as virus-specific DNA probes for B virus, as they will hybridize with B virus DNA and not DNA of any of the other primate α-herpes viruses. Such a probe PBS (SEQ ID NO:3:) which is specific for the B virus gB gene sequence is used in the present invention. Such probes also provide another approach for detection of B virus DNA in clinical and/or laboratory samples.

The amino acid sequences of the gB protein (UL27) (SEQ ID NO:6:) and a portion (SEQ ID NO:5:) of an ICP 18.5 kilodalton polypeptide (UL28) are generated by translating the sequence of the DNA segment (SEQ ID NO:4:). Knowing these amino acid sequences and the amino acid sequences of gB proteins of primate herpes viruses closely related to monkey B virus, such as SA8 gB protein sequence (SEQ ID NO:8:) helps in analysis of which specific part of the monkey B virus DNA sequence should be used for design of DNA probes for the detection of monkey B virus DNA. In addition, the amino acid sequences themselves have immense potential use in the development of serological immunoassays which can specifically detect virus antigens and/or antibodies to B virus. One approach is to synthesize peptides which, based on the properties of the predicted amino acid sequence, are likely to be immunologically active. Such peptides can be used as substrate antigens in immunoassays to detect serum antibodies which recognize this specific peptide sequence (cf. M. L. Huang et al, *J. Virol.*, 65:5073–5079 (1991); P. Horal et al, *J. Virol.*, 65:2718–2723 (1991)). Synthetic peptides are also commonly used to produce antibodies (cf. T. F. Powdrill and J. M. Johnston, *J. Virol.*, 65:2686–2690 (1991)) against specific regions of the gB protein which are unique to one virus (such as B virus or SA8). These antibodies can then be used to develop virus-specific immunoassays for differentiation of B virus from other primate α-herpes viruses and for identification of antibodies directed against B virus in primate serum samples. Knowing a DNA sequence of the coding and flanking non-coding sequences of a gene also permits the gene to be cloned into an expression vector to produce large quantities of the protein (C. C. L. Case et al, *J. Virol.*, 70:1561–1569 (1989); S. vanDrunen Littel-vandenHurk et al, *J. Virol.*, 63:2159–2168 (1989); D. A. R. Fitzpatrick et al, *Virol.*, 176:145–157 (1990)). This approach can also be used to produce large amounts of the B virus gB protein or portions of it for use in virus-specific immunoassays, thereby eliminating the hazards and biocontainment problems which arise when working with the infectious virus.

B virus DNA has been identified, using the methods of the present invention, in 16 out of 30 samples whereas only 11 of those 30 specimens were shown to be positive by virus isolation. This difference in results can be ascribed either to the low infectious virus titer present in the test specimens that could be a limiting factor in the viral culture isolation or to the advantage of the methods of the present invention in which the starting DNA template is amplified in the magnitude of $10^5$ to $10^7$ fold.

The methods of the present invention can also be used in the detection and control of B virus infections in macaque colonies. Identification of B virus shedding in infected macaques is an important step towards prevention of human B virus infections. These methods can be used as a reliable technique to monitor viral shedding in the absence of visible lesions in infected individuals, thus improving the understanding of the epidemiology and the pathogenesis of B virus infection. Furthermore, these methods can be a useful tool in the evaluation of antiviral drugs both in natural hosts and in B virus infected human patients receiving antiviral therapy.

B virus DNA from both human and monkey samples has been successfully detected using the methods of the present invention. The specificity of the primers BV1 (SEQ ID NO:1:) and BV2 (SEQ ID NO:2:) in the amplification of B virus DNA was demonstrated by Southern blot hybridization with an internal oligonucleotide probe PB 5(SEQ ID NO:3:) and by digestion of PCR products with Sac II restriction enzyme. The specificity of sense primers B3 ((SEQ ID NO:9:) or (SEQ ID NO:11:)) and antisense primers B4( (SEQ ID NO:10:) or B4' (SEQ ID NO:12:)) has also been demonstrated by digestion of PCR products with Hae III restriction enzyme.

Minor sequence variation is known to exist among different strains of a given virus, and such variation has been observed between DNA sequences of several HSV1 strains (E. J. Bzik, *Virol.*, 133:301–314 (1984); P. E. Pellett et al, *J. Virol.*, 53:243–253 (1985); L. L. Stuve et al, *J. Virol.*, 61:326–335 (1987)). By the same token, the use of sequences as primers which have minor sequence variations but are at least 90% homologous with selected sequences in the monkey B virus DNA segments (SEQ ID NO:4:) can also be effective as primers in applying the methods of the present invention to detect the presence of monkey B virus DNA in a sample.

EXAMPLES

Example 1

Viruses, cells and plasmids

The E2490 strain of B virus, originally isolated from rhesus monkeys, was used. The virus was propagated and titered on CV-1 monkey kidney cells or Vero cells as described (R. Eberle and J. K. Hilliard (1984)). The pKBXX plasmid containing the HSV1 (KOS) gB gene coding sequences and 300–500 base pairs of 3' and 5' flanking sequences cloned into pBR322 (D. J. Bzik et al (1984) was kindly provided by Dr. S. Person (University of Pittsburgh Medical School).

Example 2

Recombinant DNA methods

B virus and SA8 DNA was purified from infected cells using the procedure of Walboomers and terSchagget (J. M. Walboomers, J.terSchagget (1976)). All cloning was done using the pUC19 (pLH1 and pBluescript® vectors) vector and recombinant plasmids were grown in DH5 α cells (BRL) using standard methods (T. Maniatis, E. F. Fritsch, J. Sambrook (1982)). Plasmid DNAs were isolated using an alkaline lysis miniprep method. Restriction fragments for subcloning were electroeluted from agarose gels (Molecular Biology Grade, BioRad Laboratories) prior to ligation with pUC 19. Hybridizations were performed at 60° C. for HSV1-SA8 hybridizations or at 80° C. for SA8-SA8 hybridizations (J. K. Hilliard, D. Black, R. Eberle (1989)).

Example 3

DNA sequencing

Forward and reverse pUC primers were purchased from Promega Biotech and synthetic primers were purchased from National Biosciences, Inc. (Madison, Wis.). Samples were electrophoresed on 6–7.5% acrylamide/8M urea gels, dried, and autoradiography performed using Kodak XAR-5 film.

The majority of the sequence data reported here was derived from sequencing of both strands. This included all areas in which there was significant divergence from the HSV sequence and all areas where repeated sequencing failed to give consistent results. The few areas where both strands were not sequenced were sequenced multiple times yielding consistent results and constituted conserved regions of the gB gene. The nucleotide sequence data reported in this paper have been deposited in the GenBank nucleotide sequence database (accession number M57388).

Example 4

Sequence analysis

DNA sequences were assembled and translated using the IBI Pustell programs (International Biotechnologies, Inc., New Haven, Conn.). Alignments and secondary structural predictions for polypeptides were performed on a VAX 6320 at the Pittsburgh Supercomputing Center using the UWGCG programs. Multiple pairwise sequence comparisons and hierarchical cluster analysis were performed using the program MULTALIN of Corpet (F. Corpet (1988)).

Example 5

Viral DNA

Viral stocks and viral DNA of B virus (strain E2490), HSV1 (strain KOS), and HSV2 (strain 186) were prepared as previously described (Hilliard et al (1986)). In addition, B virus strains isolated in the laboratory from an infected human and from three infected monkeys were used.

Example 6

Preparation of monkey samples

Samples from twelve B virus seropositive and three seronegative monkeys were used. Ocular, buccal or genital swabs were resuspended in one ml of Hank's modified essential medium. 100 μl aliquots of each sample were centrifuged and washed twice in PBS for cell collection. Each sample pellet was incubated for three hours at 55° C. in 100 μl of lysis buffer (50 mM Tris, 1 mM EDTA, 0.5% Tween 20) containing 400 μl/ml proteinase K. The samples were incubated at 95° C. for 10 minutes to inactivate the proteinase K and 30–50 μl of the supernatant was used for amplification.

Example 7

Preparation of human samples

Swab samples from wounds or lesions of five humans working with macaque monkeys and from a B virus seropositive human in therapeutic treatment with acyclovir were processed as described above. DNAs from frozen autopsy samples collected following death of four humans from B virus infection were phenol-chloroform extracted followed by proteinase K digestion.

Example 8

PCR assay

Two 21-base pair oligonucleotide primers, BV1 (SEQ ID NO:1:) and BV2 (SEQ ID NO:2:), were synthesized from a portion (SEQ ID NO:5:) of the ICP 18.5 (UL 28) gene of B virus (R. Eberle, D. Black, J. K. Hilliard, unpublished data). This primer set amplifies a 128 base pairs fragment of B virus and HSV1 and a 125 base pairs fragment of HSV2. The internal oligonucleotide probe (22 mer), PB5 (SEQ ID NO:3:) was selected for its B virus sequence specificity, having a 4 and 5 base pairs mismatch with the amplified HSV1 and the two primer DNA sequences (sense primer BV1 (SEQ ID NO:1:) and antisense primer BV2 (SEQ ID NO :2:)), respectively. The sequences of the primers (sense primer B3 (SEQ ID NO:9:) or sense primer B3' (SEQ ID NO:11:)) and (antisense primer B4 (SEQ ID NO:10:) or antisense primer B4' (SEQ ID NO:12:)) are also listed in Table 1.

TABLE 1

Oligonucleotide sequences of primers and probe to amplify B virus

| | Sequence | Orientation |
|---|---|---|
| BV1 (SEQ ID NO:1:) | 5' ACC TCA CGT ACG ACT CCG ACT 3' | Sense |
| BV2 (SEQ ID NO:2:) | 5' CTG CAG GAC CGA GTA GAG GAT 3' | Antisense |
| PB5 (SEQ ID NO:3:) | 5' GGA GAA GAC GTC GCG GTC GTA C 3' | Probe |
| B3 (SEQ ID NO:9:) | 5' TTC ACC GTG GCC TGG GAC TGG 3' | Sense |
| B3' (SEQ ID NO:11:) | 5' TTC ACC GTG GGC TGG GAC TGG 3' | Sense |
| B4 (SEQ ID NO:10:) | 5' GCG ATT CTG CAG CTC GCA CCA 3' | Antisense |
| B4' (SEQ ID NO:12:) | 5' GCG GTT CTG GAG CTC GCA CCA 3' | Antisense |

Amplification was carried out in a 100 μl reaction mixture containing 10 mmol/l Tris-HCl pH 8.3, 50 mmol/l KCl, 2 mmol MgCl$_2$, 200 μmol/l of each dNTP, 150 pmol of each primer and 2.5 units of Taq DNA polymerase (Perkin-Elmer Cetus). The reaction mix was covered with three drops of mineral oil and subjected, after an initial denaturation step at 94° C. for 5 minutes to 30 cycles of amplification using a DNA Thermal Cycler (Perkin-Elmer Cetus). Each cycle consisted of a denaturation step of the DNA template at 94° C. for 1 minute, primer-template annealing at 56° C. for 1 minute, and DNA synthesis at 72° C. for 1 minute. To prevent carryover of amplified DNA sequences, samples were prepared in a separate laboratory from that in which the reactions were performed. Since the barrel of pipetting devices can become contaminated with aerosols containing sample DNA, aerosol resistant tips (Continental Laboratory Products) were used. Moreover, internal controls that contained all the components of the reaction mixture except the template DNA were included in order to assess possible contamination during PCR preparation. These controls were assembled both during and after all other polymerase chain reactions had been set up.

Example 9

Analysis of PCR products

For each sample, 20 μl of the amplified DNA product before or after digestion with Sac II restriction enzyme (Promega) was fractionated by 4% agarose gel electrophoresis (Nu Sieve 3:1, FMC), stained with ethidium bromide and transferred to a nylon membrane in alkaline buffer for Southern blot hybridization as recommended by the manufacturer (Schleicher & Schuell). The membrane was prehybridized at 42° C. for 1 hour in 5× SSC (1× SSC=0.15 mol/l sodium chloride, 0.015 mol/l sodium citrate), 5% Denhardt's solution (1×=0.02% bovine serum albumin, 0.02% Ficoll, 0.02% polyvinylpyrrolidone), 1% sodium dodecyl sulphate (SDS) and 100 μg/ml denatured salmon sperm DNA. Hybridization was carried out at 66° C. for 3 hours with an end-labeled-gamma-$^{32}$P-ATP oligonucleotide probe PB5 (SEQ ID NO:3:) in 5× SSC, 1% SDS and 100 μg/ml denatured salmon sperm DNA. The membranes were washed in 2× SSC, 1% SDS three times at room temperature for 10 minutes, then twice at 66° C. for 15 minutes in 1× SSC, 1% SDS and a final wash in 0.1× SSC, 1% SDS at 67° C. for 5 minutes. The membranes were then exposed to X-ray film (Kodak X-Omat) for 4–16 hours at –70° C.

Example 10

Analysis of specificity of the PCR assay on control samples

A fragment of about 128 base pairs of B virus, HSV1 and HSV2 DNA was successfully amplified using the BV1 (SEQ ID NO:1:) and BV2 (SEQ ID NO:2:) primers. The ability of this set of primers to amplify the expected fragment was verified in four B virus isolates from three infected monkeys and one human B virus isolate. In order to unequivocally discriminate between DNA amplified from B virus versus HSV, the amplification product was analyzed by restriction enzyme analysis or by Southern blot hybridization using an end-labeled oligonucleotide internal probe specific for the amplified B virus DNA. Sac II was the restriction enzyme of choice since it does not cut the HSV1 and HSV2 products while amplified B virus sequence should have a single cleavage site which will yield two fragments of about 72 and 56 base pairs, respectively. The Sac II pattern clearly distinguished different B virus isolates from both HSV types (FIG. 1). Hybridization of PCR products with the $^{32}$P-end-labeled oligonucleotide probe PB5 yielded a highly specific signal in B virus amplified products but no cross-hybridization with HSV1 or HSV2 amplified products (data not shown). In the case of the second primer set B3 ((SEQ ID NO:9:) or (SEQ ID NO:11:)) and B4 ((SEQ ID NO:10:) or (SEQ ID NO:12:)), Hae III was used to differentiate the B virus PCR amplimer from those of HSV-1, HSV-2 and SA8.

Example 11

Human samples

Figure 2:
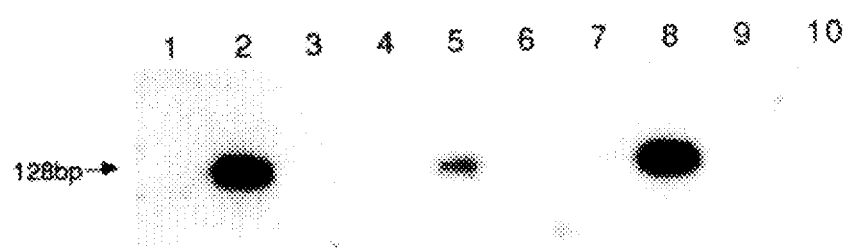

DNA extracted from frozen autopsy tissues of two B virus casualties and swab samples of the lesions from one B virus antibody positive and five suspect B virus infected humans were investigated by PCR followed by Southern blot hybridization. Southern blot hybridization of PCR products showed the presence of B virus in seven out of nine autopsy tissues investigated, whereas the swab samples investigated were negative (FIG. 2). However, one swab sample obtained from a buccal lesion of a monkey handler contained HSV related-nucleotide sequences as determined by ethidium bromide staining before and after Sac II restriction analysis. This was later confirmed by isolation of HSV1 from the swab sample. The PCR results were retrospectively compared with those for virus isolation. All the samples positive for B virus by culture were also positive by PCR. However, two samples were positive only by PCR, suggesting that the PCR assay is more sensitive.

Example 12

Monkey swab samples

Of the 15 monkeys used in this study, 12 had B virus antibody titers by ELISA. Specimens obtained from 3 serologic negative monkeys were negative for B virus infection by PCR, as well as by virus culture. Swabs from 9 out of 12 antibody positive monkeys (primarily buccal swab specimens) were positive by PCR whereas only 6 were positive by virus culture.

While the foregoing invention has been described in some detail for purposes of clarity and understanding, it will be cleared to one skilled in the art from the reading of this disclosure that various changes in form and detail can be made without departing from the true scope of the invention.

---

What is claimed is:

1. A substantially pure form of a DNA sequence of heroes simian monkey B virus comprising (SEQ ID NO:4:), said DNA coding for a gB glycoprotein comprising (SEQ ID NO:6:) and a polypeptide comprising (SEQ ID NO:5:).

2. A gB glycoprotein of herpes simian monkey B virus comprising (SEQ ID NO:6:).

3. A recombinant DNA molecule comprising:
a) a substantially pure DNA sequence of herpes simian monkey B virus comprising (SEQ ID NO:4:); and
b) a vector for introducing the DNA sequence into a host cell.

\* \* \* \* \*

UNITED STATES PATENT AND TRADEMARK OFFICE
CERTIFICATE OF CORRECTION

PATENT NO. : 5,767,265  
APPLICATION NO. : 08/541878  
DATED : June 16, 1998  
INVENTOR(S) : Richard Eberle et al.

Page 1 of 1

It is certified that error appears in the above-identified patent and that said Letters Patent is hereby corrected as shown below:

Column 1, Lines 5-8

Delete

"The work leading to the present invention was partially supported by National Institutes of Health Grants Nos. P40 RR05162 and 401 RR03163. The U.S. Government may hold rights in the present patent."

replace with

"This invention was made with government support under Grant Numbers RR05162 and RR03163 awarded by the National institutes of Health. The government has certain rights in the invention."

Signed and Sealed this  
Ninth Day of October, 2012

David J. Kappos  
*Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:1:

```
ACCTCACGTA CGACTCCGAC T                                                                          21
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:2:

```
CTGCAGGACC GAGTAGAGGA T                                                                          21
```

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:3:

```
GGAGAAGACG TCGCGGTCGT AC                                                                         22
```

( 2 ) INFORMATION FOR SEQ ID NO:4:

( i ) SEQUENCE CHARACTERISTICS:
        ( A ) LENGTH: 3177 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: CDS
        ( B ) LOCATION: 269..2941

( i x ) FEATURE:
        ( A ) NAME/KEY: CDS
        ( B ) LOCATION: 1..249

( x i ) SEQUENCE DESCRIPTION: SEQ ID NO:4:

```
AGT CGA GTG GGG CGG CCC GAC TAC GGT CGG CCC ACC CCC GAG GGG GTC            48
Ser Arg Val Gly Arg Pro Asp Tyr Gly Arg Pro Thr Pro Glu Gly Val
 1               5                  10                  15

TAC CGC TAC CCC CCG GGC GTG TAC CTC ACG TAC GAC TCC GAC TGC CCG            96
Tyr Arg Tyr Pro Pro Gly Val Tyr Leu Thr Tyr Asp Ser Asp Cys Pro
                20                  25                  30

CTG GTG GCC ATC GTC GAG TGC GAG CCG GAC GGC GGC ATC GGC CCG CGG           144
Leu Val Ala Ile Val Glu Cys Glu Pro Asp Gly Gly Ile Gly Pro Arg
             35                  40                  45

TCG GTC GTG GTG TAC GAC CGC GAC GTC TTC TCC ATC CTC TAC TCG GTC           192
Ser Val Val Val Tyr Asp Arg Asp Val Phe Ser Ile Leu Tyr Ser Val
 50                  55                  60

CTG CAG CAC CTG GCC CCC AGG CTC GCG GCC GGG GGG CCC GAC CAG CCG           240
Leu Gln His Leu Ala Pro Arg Leu Ala Ala Gly Gly Pro Asp Gln Pro
 65                  70                  75                  80

CCC CCG TAGCCGCCCG CGCGCCGCGG GG ATG CGG CCC CGC GCC GGC CCC CTC          292
Pro Pro                          Met Arg Pro Arg Ala Gly Pro Leu
                                   1               5

CCC CTC CCC TCC CCC CTC GTC CCC CTC CTG GCC CTC GCC CTC CTC GCC           340
Pro Leu Pro Ser Pro Leu Val Pro Leu Leu Ala Leu Ala Leu Leu Ala
         10                  15                  20
```

| | | | | | | | | | | | | | | | | |
|---|---|---|---|---|---|---|---|---|---|---|---|---|---|---|---|---|
| GCG | ACC | CGG | CCG | CTG | GGC | CCC | GCG | GCG | GCG | ACC | CCC | GTG | GTG | AGC | CCG | 388 |
| Ala | Thr | Arg | Pro | Leu | Gly | Pro | Ala | Ala | Ala | Thr | Pro | Val | Val | Ser | Pro | |
| 25 | | | | 30 | | | | | 35 | | | | | | 40 | |
| CGG | GCC | TCT | CCG | GCC | CCG | CCC | GTC | CCC | GCG | GCC | ACG | CCG | ACG | TTT | CCA | 436 |
| Arg | Ala | Ser | Pro | Ala | Pro | Pro | Val | Pro | Ala | Ala | Thr | Pro | Thr | Phe | Pro | |
| | | | | 45 | | | | | 50 | | | | | 55 | | |
| GAT | GAC | GAT | AAC | GAT | GGC | GAG | GCC | GGG | GCC | GCG | CCG | GGC | GCG | CCG | GGC | 484 |
| Asp | Asp | Asp | Asn | Asp | Gly | Glu | Ala | Gly | Ala | Ala | Pro | Gly | Ala | Pro | Gly | |
| | | | 60 | | | | 65 | | | | | 70 | | | | |
| ACC | AAC | GCG | TCC | GTC | GAG | GCC | GGC | CAC | GCG | ACG | CTG | CGG | GAG | AAC | CTG | 532 |
| Thr | Asn | Ala | Ser | Val | Glu | Ala | Gly | His | Ala | Thr | Leu | Arg | Glu | Asn | Leu | |
| | | 75 | | | | | 80 | | | | | 85 | | | | |
| CGG | GAC | ATC | AAG | GCC | CTG | GAC | GGC | GAC | GCG | ACC | TTC | TAC | GTC | TGC | CCG | 580 |
| Arg | Asp | Ile | Lys | Ala | Leu | Asp | Gly | Asp | Ala | Thr | Phe | Tyr | Val | Cys | Pro | |
| | 90 | | | | | 95 | | | | 100 | | | | | | |
| CCG | CCG | ACC | GGC | GCC | ACG | GTG | GTG | CAG | TTT | GAG | CAG | CCC | CGG | CCG | TGC | 628 |
| Pro | Pro | Thr | Gly | Ala | Thr | Val | Val | Gln | Phe | Glu | Gln | Pro | Arg | Pro | Cys | |
| 105 | | | | | 110 | | | | | 115 | | | | | 120 | |
| CCG | CGG | GCG | CCC | CAC | GGC | CAG | AAC | TAC | ACC | GAG | GGG | ATC | GCG | GTG | ATC | 676 |
| Pro | Arg | Ala | Pro | His | Gly | Gln | Asn | Tyr | Thr | Glu | Gly | Ile | Ala | Val | Ile | |
| | | | | 125 | | | | | 130 | | | | | 135 | | |
| TTC | AAG | GAG | AAC | ATC | GCC | CCG | TAC | AAG | TTC | AAG | GCC | ACC | ATG | TAC | TAC | 724 |
| Phe | Lys | Glu | Asn | Ile | Ala | Pro | Tyr | Lys | Phe | Lys | Ala | Thr | Met | Tyr | Tyr | |
| | | | 140 | | | | 145 | | | | | 150 | | | | |
| AAG | GAC | GTG | ACC | GTC | TCG | CAG | GTC | TGG | TTC | GGC | CAC | AGG | TAC | TCG | CAG | 772 |
| Lys | Asp | Val | Thr | Val | Ser | Gln | Val | Trp | Phe | Gly | His | Arg | Tyr | Ser | Gln | |
| | | 155 | | | | | 160 | | | | | 165 | | | | |
| TTC | ATG | GGG | ATC | TTC | GAG | GAC | CGC | GCC | CCC | GTG | CCC | TTC | GAG | GAG | GTG | 820 |
| Phe | Met | Gly | Ile | Phe | Glu | Asp | Arg | Ala | Pro | Val | Pro | Phe | Glu | Glu | Val | |
| | 170 | | | | | 175 | | | | | 180 | | | | | |
| ATC | GAC | AAG | ATC | AAC | GCC | AGG | GGG | GTC | TGC | CGC | TCG | ACG | GCA | AAG | TAC | 868 |
| Ile | Asp | Lys | Ile | Asn | Ala | Arg | Gly | Val | Cys | Arg | Ser | Thr | Ala | Lys | Tyr | |
| 185 | | | | | 190 | | | | | 195 | | | | | 200 | |
| GTG | CGG | AAC | AAC | ATG | GAG | AGC | ACG | GCG | TTC | CAC | CGC | GAC | GAC | GAC | GAG | 916 |
| Val | Arg | Asn | Asn | Met | Glu | Ser | Thr | Ala | Phe | His | Arg | Asp | Asp | Asp | Glu | |
| | | | | 205 | | | | | 210 | | | | | 215 | | |
| TCG | GAC | ATG | AAG | CTG | AAG | CCC | GCG | AAG | GCC | GCG | ACC | CGC | ACC | AGC | CGC | 964 |
| Ser | Asp | Met | Lys | Leu | Lys | Pro | Ala | Lys | Ala | Ala | Thr | Arg | Thr | Ser | Arg | |
| | | | 220 | | | | 225 | | | | | 230 | | | | |
| GGC | TGG | CAC | ACC | ACC | GAC | CTG | AAG | TAC | AAC | CCC | TCG | CGG | ATC | GAG | GCG | 1012 |
| Gly | Trp | His | Thr | Thr | Asp | Leu | Lys | Tyr | Asn | Pro | Ser | Arg | Ile | Glu | Ala | |
| | | 235 | | | | | 240 | | | | | 245 | | | | |
| TTC | CAC | CGC | TAC | GGC | ACC | ACG | GTG | AAC | TGC | ATC | GTC | GAG | GAG | GTG | GAG | 1060 |
| Phe | His | Arg | Tyr | Gly | Thr | Thr | Val | Asn | Cys | Ile | Val | Glu | Glu | Val | Glu | |
| | 250 | | | | | 255 | | | | | 260 | | | | | |
| GCC | CGC | TCG | GTG | TAC | CCG | TAC | GAC | GAG | TTC | GTG | CTG | GCG | ACC | GGG | GAC | 1108 |
| Ala | Arg | Ser | Val | Tyr | Pro | Tyr | Asp | Glu | Phe | Val | Leu | Ala | Thr | Gly | Asp | |
| 265 | | | | | 270 | | | | | 275 | | | | | 280 | |
| TTT | GTG | TAC | ATG | TCG | CCG | TTC | TAC | GGC | TAC | CGC | GAC | GGG | GCC | CAC | GCC | 1156 |
| Phe | Val | Tyr | Met | Ser | Pro | Phe | Tyr | Gly | Tyr | Arg | Asp | Gly | Ala | His | Ala | |
| | | | | 285 | | | | | 290 | | | | | 295 | | |
| GAG | CAC | ACG | GCC | TAC | GCC | GCG | GAC | CGC | TTT | CGG | CAG | GTG | GAC | GGC | TAC | 1204 |
| Glu | His | Thr | Ala | Tyr | Ala | Ala | Asp | Arg | Phe | Arg | Gln | Val | Asp | Gly | Tyr | |
| | | | 300 | | | | 305 | | | | | 310 | | | | |
| TAC | GAG | CGC | GAC | CTC | TCC | ACG | GGG | CGG | CGC | GCC | TCC | ACG | CCG | GCG | ACG | 1252 |
| Tyr | Glu | Arg | Asp | Leu | Ser | Thr | Gly | Arg | Arg | Ala | Ser | Thr | Pro | Ala | Thr | |
| | | 315 | | | | | 320 | | | | | 325 | | | | |
| CGC | AAC | CTC | CTG | ACC | ACC | CCC | AAG | TTC | ACC | GTG | GGC | TGG | GAC | TGG | GCG | 1300 |
| Arg | Asn | Leu | Leu | Thr | Thr | Pro | Lys | Phe | Thr | Val | Gly | Trp | Asp | Trp | Ala | |
| | 330 | | | | | 335 | | | | | 340 | | | | | |

| | | | | | | | | | | | | | | | | |
|---|---|---|---|---|---|---|---|---|---|---|---|---|---|---|---|---|
| CCC | AAG | CGC | CCC | TCG | GTC | TGC | ACG | CTG | ACC | AAG | TGG | CAG | GAG | GTG | GAC | 1348 |
| Pro 345 | Lys | Arg | Pro | Ser 350 | Val | Cys | Thr | Leu | Thr 355 | Lys | Trp | Gln | Glu | Val 360 | Asp | |
| GAG | ATG | CTG | CGC | GCC | GAG | TAC | GGC | CCC | TCG | TTC | CGC | TTC | TCC | TCG | TCC | 1396 |
| Glu | Met | Leu | Arg 365 | Ala | Glu | Tyr | Gly | Pro 370 | Ser | Phe | Arg | Phe | Ser 375 | Ser | Ser | |
| GCC | CTC | TCC | ACC | ACC | TTC | ACG | ACC | AAC | CGC | ACC | GAG | TAC | GCC | CTG | TCG | 1444 |
| Ala | Leu | Ser 380 | Thr | Thr | Phe | Thr | Thr | Asn 385 | Arg | Thr | Glu | Tyr | Ala 390 | Leu | Ser | |
| CGC | GTC | GAC | CTC | GGG | GAC | TGC | GTC | GGG | CGC | GAG | GCC | CGA | GAG | GCC | GTG | 1492 |
| Arg | Val 395 | Asp | Leu | Gly | Asp | Cys 400 | Val | Gly | Arg | Glu | Ala 405 | Arg | Glu | Ala | Val | |
| GAC | CGC | ATC | TTC | CTC | CGG | CGC | TAC | AAC | GGC | ACG | CAC | GTG | AAG | GTG | GGC | 1540 |
| Asp | Arg 410 | Ile | Phe | Leu | Arg | Arg 415 | Tyr | Asn | Gly | Thr | His 420 | Val | Lys | Val | Gly | |
| CAG | GTG | CAG | TAC | TAC | CTG | GCC | ACG | GCC | GGC | TTT | CTC | ATC | GCG | TAC | CAG | 1588 |
| Gln 425 | Val | Gln | Tyr | Tyr | Leu 430 | Ala | Thr | Ala | Gly | Phe 435 | Leu | Ile | Ala | Tyr | Gln 440 | |
| CCC | CTC | CTC | AGC | AAC | GGG | CTC | GTG | GAG | CTG | TAC | GTG | CGG | GAG | CTC | CTC | 1636 |
| Pro | Leu | Leu | Ser | Asn 445 | Gly | Leu | Val | Glu | Leu 450 | Tyr | Val | Arg | Glu | Leu 455 | Leu | |
| CGC | GAG | CAG | GAG | GGC | CGG | CCG | GGC | GAC | GCG | GCG | GCG | ACC | CCG | AAG | CCC | 1684 |
| Arg | Glu | Gln | Glu 460 | Gly | Arg | Pro | Gly | Asp 465 | Ala | Ala | Ala | Thr | Pro 470 | Lys | Pro | |
| TCC | GCC | GAC | CCC | CCC | GAC | GTG | GAG | CGC | ATC | AAG | ACC | ACG | TCC | TCG | GTC | 1732 |
| Ser | Ala | Asp 475 | Pro | Pro | Asp | Val | Glu 480 | Arg | Ile | Lys | Thr | Thr 485 | Ser | Ser | Val | |
| GAG | TTC | GCG | CGC | CTG | CAG | TTC | ACG | TAC | GAC | CAC | ATC | CAG | CGG | CAC | GTC | 1780 |
| Glu | Phe 490 | Ala | Arg | Leu | Gln | Phe 495 | Thr | Tyr | Asp | His | Ile 500 | Gln | Arg | His | Val | |
| AAC | GAC | ATG | CTG | GGG | CGC | ATC | GCC | ATC | GCC | TGG | TGT | GAG | CTC | CAG | AAC | 1828 |
| Asn 505 | Asp | Met | Leu | Gly | Arg 510 | Ile | Ala | Ile | Ala | Trp 515 | Cys | Glu | Leu | Gln | Asn 520 | |
| CAC | GAG | CTG | ACG | CTG | TGG | AAC | GAG | GCC | CGC | AAG | CTG | AAC | CCC | AAC | GCC | 1876 |
| His | Glu | Leu | Thr | Leu 525 | Trp | Asn | Glu | Ala | Arg 530 | Lys | Leu | Asn | Pro | Asn 535 | Ala | |
| ATC | GCC | TCG | GCC | ACC | GTC | GGC | CGC | CGG | GTG | AGC | GCG | CGG | ATG | CTC | GGG | 1924 |
| Ile | Ala | Ser | Ala 540 | Thr | Val | Gly | Arg | Arg 545 | Val | Ser | Ala | Arg | Met 550 | Leu | Gly | |
| GAC | GTG | ATG | GCC | GTC | TCC | ACC | TGC | GTG | CCC | GTG | ACC | CCC | GAC | AAC | GTC | 1972 |
| Asp | Val | Met 555 | Ala | Val | Ser | Thr | Cys 560 | Val | Pro | Val | Thr | Pro 565 | Asp | Asn | Val | |
| ATC | ATG | CAG | AAC | TCG | ATG | CGC | GTC | CCC | GCG | CGC | CCC | GGG | ACG | TGC | TAC | 2020 |
| Ile | Met | Gln 570 | Asn | Ser | Met | Arg | Val 575 | Pro | Ala | Arg | Pro | Gly 580 | Thr | Cys | Tyr | |
| AGC | CGC | CCC | CTG | GTC | AGC | TTC | CGC | TAC | GAG | GAG | GGC | GGG | CCC | CTG | GTC | 2068 |
| Ser 585 | Arg | Pro | Leu | Val | Ser 590 | Phe | Arg | Tyr | Glu | Glu 595 | Gly | Gly | Pro | Leu | Val 600 | |
| GAG | GGC | CAG | CTG | GGC | GAG | GAC | AAC | GAG | ATC | CGC | CTC | GAG | CGC | GAC | GCC | 2116 |
| Glu | Gly | Gln | Leu | Gly 605 | Glu | Asp | Asn | Glu | Ile 610 | Arg | Leu | Glu | Arg | Asp 615 | Ala | |
| CTC | GAG | CCC | TGC | ACC | GTC | GGT | CAC | CGG | CGC | TAC | TTC | ACC | TTC | GGG | GCG | 2164 |
| Leu | Glu | Pro | Cys 620 | Thr | Val | Gly | His | Arg 625 | Arg | Tyr | Phe | Thr | Phe 630 | Gly | Ala | |
| GGC | TAC | GTG | TAC | TTT | GAG | GAT | TAC | GCG | TAC | TCC | CAC | CAG | CTG | GGT | CGC | 2212 |
| Gly | Tyr | Val 635 | Tyr | Phe | Glu | Asp | Tyr 640 | Ala | Tyr | Ser | His | Gln 645 | Leu | Gly | Arg | |
| GCC | GAC | GTG | ACC | ACG | GTC | AGC | ACG | TTC | ATC | AAC | CTC | AAC | CTC | ACG | ATG | 2260 |
| Ala | Asp | Val 650 | Thr | Thr | Val | Ser | Thr 655 | Phe | Ile | Asn | Leu | Asn 660 | Leu | Thr | Met | |

-continued

| | | | | | | | | | | | | | | | |
|---|---|---|---|---|---|---|---|---|---|---|---|---|---|---|---|
| CTC | GAG | GAC | CAC | GAG | TTC | GTG | CCC | CTG | GAG | GTC | TAC | ACC | CGC | CAG | GAG | 2308
| Leu | Glu | Asp | His | Glu | Phe | Val | Pro | Leu | Glu | Val | Tyr | Thr | Arg | Gln | Glu |
| 665 | | | | 670 | | | | | 675 | | | | | | 680 |
| ATC | AAG | GAC | AGC | GGG | CTG | CTG | GAC | TAC | ACC | GAG | GTC | CAG | CGC | CGC | AAC | 2356
| Ile | Lys | Asp | Ser | Gly | Leu | Leu | Asp | Tyr | Thr | Glu | Val | Gln | Arg | Arg | Asn |
| | | | | 685 | | | | | 690 | | | | | 695 | |
| CAG | CTC | CAC | GCG | CTC | CGC | TTC | GCC | GAC | ATC | GAC | ACG | GTC | ATC | AAG | GCC | 2404
| Gln | Leu | His | Ala | Leu | Arg | Phe | Ala | Asp | Ile | Asp | Thr | Val | Ile | Lys | Ala |
| | | | 700 | | | | | 705 | | | | | 710 | | |
| GAC | GCG | CAC | GCG | CCG | CTG | TTC | GCG | GGC | CTC | TAC | TCC | TTC | TTC | GAG | GGC | 2452
| Asp | Ala | His | Ala | Pro | Leu | Phe | Ala | Gly | Leu | Tyr | Ser | Phe | Phe | Glu | Gly |
| | | 715 | | | | | 720 | | | | | 725 | | | |
| CTC | GGG | GAC | GTG | GGC | CGC | GCG | GTC | GGC | AAG | GTC | GTC | ATG | GGC | ATC | GTG | 2500
| Leu | Gly | Asp | Val | Gly | Arg | Ala | Val | Gly | Lys | Val | Val | Met | Gly | Ile | Val |
| | 730 | | | | | 735 | | | | | 740 | | | | |
| GGG | GGC | GTC | GTC | TCC | GCC | GTC | TCG | GGC | GTG | TCC | TCC | TTC | CTC | TCC | AAC | 2548
| Gly | Gly | Val | Val | Ser | Ala | Val | Ser | Gly | Val | Ser | Ser | Phe | Leu | Ser | Asn |
| 745 | | | | | 750 | | | | | 755 | | | | | 760 |
| CCC | TTC | GGG | GCC | CTG | GCC | GTC | GGG | CTG | CTG | GTC | CTG | GCC | GGG | CTG | GCG | 2596
| Pro | Phe | Gly | Ala | Leu | Ala | Val | Gly | Leu | Leu | Val | Leu | Ala | Gly | Leu | Ala |
| | | | | 765 | | | | | 770 | | | | | 775 | |
| GCG | GCC | TTC | TTC | GCC | TTC | CGC | TAC | GTC | ATG | CGC | CTG | CAG | CGC | AAC | CCC | 2644
| Ala | Ala | Phe | Phe | Ala | Phe | Arg | Tyr | Val | Met | Arg | Leu | Gln | Arg | Asn | Pro |
| | | | 780 | | | | | 785 | | | | | 790 | | |
| ATG | AAG | GCC | CTG | TAC | CCG | CTG | ACC | ACC | AAG | GAG | CTC | AAG | AGC | GAC | GGG | 2692
| Met | Lys | Ala | Leu | Tyr | Pro | Leu | Thr | Thr | Lys | Glu | Leu | Lys | Ser | Asp | Gly |
| | | 795 | | | | | 800 | | | | | 805 | | | |
| CCG | TCG | CGC | GGC | GAC | GGC | GGG | GAC | GGC | GCC | TCC | GGG | GGC | GGC | GAG | GAG | 2740
| Pro | Ser | Arg | Gly | Asp | Gly | Gly | Asp | Gly | Ala | Ser | Gly | Gly | Gly | Glu | Glu |
| | 810 | | | | | 815 | | | | | 820 | | | | |
| GAC | TTC | GAC | GAG | GCC | AAG | CTG | GCG | CAG | GCG | CGG | GAG | ATG | ATA | CGC | TAC | 2788
| Asp | Phe | Asp | Glu | Ala | Lys | Leu | Ala | Gln | Ala | Arg | Glu | Met | Ile | Arg | Tyr |
| 825 | | | | 830 | | | | | 835 | | | | | 840 | |
| ATG | GCC | CTG | GTG | TCG | GCC | ATG | GAG | CGC | ACG | GAG | CAC | AAG | GCC | CGC | AAG | 2836
| Met | Ala | Leu | Val | Ser | Ala | Met | Glu | Arg | Thr | Glu | His | Lys | Ala | Arg | Lys |
| | | | 845 | | | | | 850 | | | | | 855 | | |
| AAG | GGC | ACG | AGC | GCC | CTG | CTG | AGC | GCC | AAG | GTC | ACC | AAC | ATG | GTG | ATG | 2884
| Lys | Gly | Thr | Ser | Ala | Leu | Leu | Ser | Ala | Lys | Val | Thr | Asn | Met | Val | Met |
| | | | 860 | | | | | 865 | | | | | 870 | | |
| CGA | AAG | CGC | GCC | AAG | CCG | CGG | TAC | TCC | CCC | CTG | GGC | GAC | ACA | GAC | GAA | 2932
| Arg | Lys | Arg | Ala | Lys | Pro | Arg | Tyr | Ser | Pro | Leu | Gly | Asp | Thr | Asp | Glu |
| | | 875 | | | | | 880 | | | | | 885 | | | |
| GAG | GAG | CTA | TAGCACCCCC | GGGGGCCGAG | GCCCGCGTGT | CCGCCACGGC | | | | | | | | | 2981
| Glu | Glu | Leu | | | | | | | | | | | | | |
| | 890 | | | | | | | | | | | | | | |

| | | | | |
|---|---|---|---|---|
| CGTGCGCGAC | GGGCGTTTGT | TCGGTTAATA | AAAAAGTAAT | TAATCACATT | CCGTTGTGGA | 3041 |
| GGTCTGTTCT | CGGCTCTTGG | GGTGCGCGTG | CGCGGTCCCG | TTTCCTCCCC | CCTCACCCTC | 3101 |
| CTTCCACTCA | CTGCAACTTT | TGGAAATAGT | CGGCTGGGGC | GAAATTCGCC | CGCCGCCCGG | 3161 |
| CCTGTGGGTC | CGGGTG | | | | | 3177 |

( 2 ) INFORMATION FOR SEQ ID NO:5:

( i ) SEQUENCE CHARACTERISTICS:
       ( A ) LENGTH: 82 amino acids
       ( B ) TYPE: amino acid
       ( D ) TOPOLOGY: linear ( i i ) MOLECULE TYPE: protein ( x i ) SEQUENCE DESCRIPTION: SEQ ID NO:5:

```
Ser  Arg  Val  Gly  Arg  Pro  Asp  Tyr  Gly  Arg  Pro  Thr  Pro  Glu  Gly  Val
  1              5                        10                       15

Tyr  Arg  Tyr  Pro  Pro  Gly  Val  Tyr  Leu  Thr  Tyr  Asp  Ser  Asp  Cys  Pro
               20                       25                  30

Leu  Val  Ala  Ile  Val  Glu  Cys  Glu  Pro  Asp  Gly  Gly  Ile  Gly  Pro  Arg
          35                       40                       45

Ser  Val  Val  Val  Tyr  Asp  Arg  Asp  Val  Phe  Ser  Ile  Leu  Tyr  Ser  Val
     50                        55                       60

Leu  Gln  His  Leu  Ala  Pro  Arg  Leu  Ala  Ala  Gly  Gly  Pro  Asp  Gln  Pro
 65                      70                       75                       80

Pro  Pro
```

( 2 ) INFORMATION FOR SEQ ID NO:6:

( i ) SEQUENCE CHARACTERISTICS:
        ( A ) LENGTH: 891 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Arg  Pro  Arg  Ala  Gly  Pro  Leu  Pro  Leu  Pro  Ser  Pro  Leu  Val  Pro
  1              5                        10                       15

Leu  Leu  Ala  Leu  Ala  Leu  Leu  Ala  Ala  Thr  Arg  Pro  Leu  Gly  Pro  Ala
               20                       25                       30

Ala  Ala  Thr  Pro  Val  Val  Ser  Pro  Arg  Ala  Ser  Pro  Ala  Pro  Pro  Val
          35                       40                       45

Pro  Ala  Ala  Thr  Pro  Thr  Phe  Pro  Asp  Asp  Asn  Asp  Gly  Glu  Ala
     50                        55                       60

Gly  Ala  Ala  Pro  Gly  Ala  Pro  Gly  Thr  Asn  Ala  Ser  Val  Glu  Ala  Gly
 65                      70                       75                       80

His  Ala  Thr  Leu  Arg  Glu  Asn  Leu  Arg  Asp  Ile  Lys  Ala  Leu  Asp  Gly
               85                       90                       95

Asp  Ala  Thr  Phe  Tyr  Val  Cys  Pro  Pro  Thr  Gly  Ala  Thr  Val  Val
          100                      105                      110

Gln  Phe  Glu  Gln  Pro  Arg  Pro  Cys  Pro  Arg  Ala  Pro  His  Gly  Gln  Asn
          115                      120                      125

Tyr  Thr  Glu  Gly  Ile  Ala  Val  Ile  Phe  Lys  Glu  Asn  Ile  Ala  Pro  Tyr
     130                      135                      140

Lys  Phe  Lys  Ala  Thr  Met  Tyr  Tyr  Lys  Asp  Val  Thr  Val  Ser  Gln  Val
145                       150                      155                      160

Trp  Phe  Gly  His  Arg  Tyr  Ser  Gln  Phe  Met  Gly  Ile  Phe  Glu  Asp  Arg
                165                      170                      175

Ala  Pro  Val  Pro  Phe  Glu  Glu  Val  Ile  Asp  Lys  Ile  Asn  Ala  Arg  Gly
               180                      185                      190

Val  Cys  Arg  Ser  Thr  Ala  Lys  Tyr  Val  Arg  Asn  Asn  Met  Glu  Ser  Thr
          195                      200                      205

Ala  Phe  His  Arg  Asp  Asp  Glu  Ser  Asp  Met  Lys  Leu  Lys  Pro  Ala
     210                      215                      220

Lys  Ala  Ala  Thr  Arg  Thr  Ser  Arg  Gly  Trp  His  Thr  Thr  Asp  Leu  Lys
225                       230                      235                      240

Tyr  Asn  Pro  Ser  Arg  Ile  Glu  Ala  Phe  His  Arg  Tyr  Gly  Thr  Thr  Val
               245                      250                      255

Asn  Cys  Ile  Val  Glu  Glu  Val  Glu  Ala  Arg  Ser  Val  Tyr  Pro  Tyr  Asp
                260                      265                      270
```

| | | | | | | | | | | | | | | |
|---|---|---|---|---|---|---|---|---|---|---|---|---|---|---|
|Glu|Phe|Val|Leu|Ala|Thr|Gly|Asp|Phe|Val|Tyr|Met|Ser|Pro|Phe|Tyr|
| | |275| | | |280| | | |285| | | | |
|Gly|Tyr|Arg|Asp|Gly|Ala|His|Ala|Glu|His|Thr|Ala|Tyr|Ala|Ala|Asp|
| |290| | | | |295| | | |300| | | | |
|Arg|Phe|Arg|Gln|Val|Asp|Gly|Tyr|Tyr|Glu|Arg|Asp|Leu|Ser|Thr|Gly|
|305| | | | |310| | | |315| | | | |320|
|Arg|Arg|Ala|Ser|Thr|Pro|Ala|Thr|Arg|Asn|Leu|Leu|Thr|Thr|Pro|Lys|
| | | | |325| | | |330| | | | |335| |
|Phe|Thr|Val|Gly|Trp|Asp|Trp|Ala|Pro|Lys|Arg|Pro|Ser|Val|Cys|Thr|
| | | |340| | | |345| | | | |350| | |
|Leu|Thr|Lys|Trp|Gln|Glu|Val|Asp|Glu|Met|Leu|Arg|Ala|Glu|Tyr|Gly|
| | |355| | | |360| | | |365| | | | |
|Pro|Ser|Phe|Arg|Phe|Ser|Ser|Ala|Leu|Ser|Thr|Thr|Phe|Thr|Thr|
| |370| | | | |375| | | |380| | | | |
|Asn|Arg|Thr|Glu|Tyr|Ala|Leu|Ser|Arg|Val|Asp|Leu|Gly|Asp|Cys|Val|
|385| | | | |390| | | |395| | | | |400|
|Gly|Arg|Glu|Ala|Arg|Glu|Ala|Val|Asp|Arg|Ile|Phe|Leu|Arg|Arg|Tyr|
| | | | |405| | | |410| | | | |415| |
|Asn|Gly|Thr|His|Val|Lys|Val|Gly|Gln|Val|Gln|Tyr|Tyr|Leu|Ala|Thr|
| | | |420| | | |425| | | | |430| | |
|Ala|Gly|Phe|Leu|Ile|Ala|Tyr|Gln|Pro|Leu|Leu|Ser|Asn|Gly|Leu|Val|
| | |435| | | |440| | | | |445| | | |
|Glu|Leu|Tyr|Val|Arg|Glu|Leu|Leu|Arg|Glu|Gln|Glu|Gly|Arg|Pro|Gly|
| |450| | | | |455| | | |460| | | | |
|Asp|Ala|Ala|Ala|Thr|Pro|Lys|Pro|Ser|Ala|Asp|Pro|Pro|Asp|Val|Glu|
|465| | | | |470| | | |475| | | | |480| |
|Arg|Ile|Lys|Thr|Thr|Ser|Ser|Val|Glu|Phe|Ala|Arg|Leu|Gln|Phe|Thr|
| | | | |485| | | |490| | | | |495| |
|Tyr|Asp|His|Ile|Gln|Arg|His|Val|Asn|Asp|Met|Leu|Gly|Arg|Ile|Ala|
| | | |500| | | |505| | | | |510| | |
|Ile|Ala|Trp|Cys|Glu|Leu|Gln|Asn|His|Glu|Leu|Thr|Leu|Trp|Asn|Glu|
| | |515| | | |520| | | | |525| | | |
|Ala|Arg|Lys|Leu|Asn|Pro|Asn|Ala|Ile|Ala|Ser|Ala|Thr|Val|Gly|Arg|
| |530| | | | |535| | | | |540| | | |
|Arg|Val|Ser|Ala|Arg|Met|Leu|Gly|Asp|Val|Met|Ala|Val|Ser|Thr|Cys|
|545| | | | |550| | | |555| | | | |560|
|Val|Pro|Val|Thr|Pro|Asp|Asn|Val|Ile|Met|Gln|Asn|Ser|Met|Arg|Val|
| | | | |565| | | |570| | | | |575| |
|Pro|Ala|Arg|Pro|Gly|Thr|Cys|Tyr|Ser|Arg|Pro|Leu|Val|Ser|Phe|Arg|
| | |580| | | | |585| | | | |590| | |
|Tyr|Glu|Glu|Gly|Gly|Pro|Leu|Val|Glu|Gly|Gln|Leu|Gly|Glu|Asp|Asn|
| |595| | | | |600| | | |605| | | | |
|Glu|Ile|Arg|Leu|Glu|Arg|Asp|Ala|Leu|Glu|Pro|Cys|Thr|Val|Gly|His|
| |610| | | | |615| | | |620| | | | |
|Arg|Arg|Tyr|Phe|Thr|Phe|Gly|Ala|Gly|Tyr|Val|Tyr|Phe|Glu|Asp|Tyr|
|625| | | | |630| | | |635| | | | |640|
|Ala|Tyr|Ser|His|Gln|Leu|Gly|Arg|Ala|Asp|Val|Thr|Thr|Val|Ser|Thr|
| | | |645| | | |650| | | | |655| | |
|Phe|Ile|Asn|Leu|Asn|Leu|Thr|Met|Leu|Glu|Asp|His|Glu|Phe|Val|Pro|
| | | |660| | | |665| | | | |670| | |
|Leu|Glu|Val|Tyr|Thr|Arg|Gln|Glu|Ile|Lys|Asp|Ser|Gly|Leu|Leu|Asp|
| | |675| | | |680| | | | |685| | | |
|Tyr|Thr|Glu|Val|Gln|Arg|Arg|Asn|Gln|Leu|His|Ala|Leu|Arg|Phe|Ala|

|  | 690 |  |  |  | 695 |  |  |  | 700 |  |  |  |
|---|---|---|---|---|---|---|---|---|---|---|---|---|
| Asp<br>705 | Ile | Asp | Thr | Val | Ile<br>710 | Lys | Ala | Asp | Ala | His<br>715 | Ala | Pro | Leu | Phe | Ala<br>720 |
| Gly | Leu | Tyr | Ser | Phe<br>725 | Phe | Glu | Gly | Leu | Gly<br>730 | Asp | Val | Gly | Arg | Ala<br>735 | Val |
| Gly | Lys | Val | Val<br>740 | Met | Gly | Ile | Val | Gly<br>745 | Val | Val | Ser | Ala<br>750 | Val | Ser |
| Gly | Val | Ser<br>755 | Ser | Phe | Leu | Ser | Asn<br>760 | Pro | Phe | Gly | Ala | Leu<br>765 | Ala | Val | Gly |
| Leu | Leu<br>770 | Val | Leu | Ala | Gly | Leu<br>775 | Ala | Ala | Ala | Phe | Phe<br>780 | Ala | Phe | Arg | Tyr |
| Val<br>785 | Met | Arg | Leu | Gln | Arg<br>790 | Asn | Pro | Met | Lys | Ala<br>795 | Leu | Tyr | Pro | Leu | Thr<br>800 |
| Thr | Lys | Glu | Leu | Lys<br>805 | Ser | Asp | Gly | Pro | Ser<br>810 | Arg | Gly | Asp | Gly | Gly<br>815 | Asp |
| Gly | Ala | Ser | Gly<br>820 | Gly | Gly | Glu | Glu | Asp<br>825 | Phe | Asp | Glu | Ala | Lys<br>830 | Leu | Ala |
| Gln | Ala | Arg<br>835 | Glu | Met | Ile | Arg | Tyr<br>840 | Met | Ala | Leu | Val | Ser<br>845 | Ala | Met | Glu |
| Arg | Thr<br>850 | Glu | His | Lys | Ala | Arg<br>855 | Lys | Lys | Gly | Thr | Ser<br>860 | Ala | Leu | Leu | Ser |
| Ala<br>865 | Lys | Val | Thr | Asn | Met<br>870 | Val | Met | Arg | Lys | Arg<br>875 | Ala | Lys | Pro | Arg | Tyr<br>880 |
| Ser | Pro | Leu | Gly | Asp<br>885 | Thr | Asp | Glu | Glu | Leu<br>890 |  |  |  |  |  |  |

( 2 ) INFORMATION FOR SEQ ID NO:7:

( i ) SEQUENCE CHARACTERISTICS:
        ( A ) LENGTH: 2943 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: CDS
        ( B ) LOCATION: 87..2744

( x i ) SEQUENCE DESCRIPTION: SEQ ID NO:7:

| CTGCAGCACC | TGGCCCCCAA | GCTCGCGGCC | GGCGGGCCGG | AGTCGACGCC | CGCGTAGTCG | 60 |
|---|---|---|---|---|---|---|
| CCCGCGTAGC | GCCCGCGCGC | CCCGGG ATG | CGG CCT CGC | GGC ACC CCC | CCC TCC | 113 |
|  |  | Met Arg<br>1 | Pro Arg | Gly Thr<br>5 | Pro Pro Ser |  |

| TTT | CTT | CCC | CTC | CCC | GTC | CTC | CTC | GCC | CTC | GCC | GTG | ATC | GCC | GCG | GCC | 161 |
|---|---|---|---|---|---|---|---|---|---|---|---|---|---|---|---|---|
| Phe<br>10 | Leu | Pro | Leu | Pro<br>15 | Val | Leu | Leu | Ala | Leu<br>20 | Ala | Val | Ile | Ala | Ala<br>25 | Ala |  |

| GGA | CGA | GCC | GCC | CCC | GCG | GCG | GCG | GCG | GCC | CCG | ACC | GCC | GAC | CCC | GCC | 209 |
|---|---|---|---|---|---|---|---|---|---|---|---|---|---|---|---|---|
| Gly | Arg | Ala | Ala<br>30 | Pro | Ala | Ala | Ala | Ala<br>35 | Pro | Thr | Ala | Asp | Pro<br>40 | Ala |  |  |

| GCC | ACG | CCC | GCG | CTT | CCC | GAG | GAC | GAG | GTC | CCG | GAC | GAG | GAC | GGG | 257 |
|---|---|---|---|---|---|---|---|---|---|---|---|---|---|---|---|
| Ala | Thr | Pro | Ala<br>45 | Leu | Pro | Glu | Asp | Glu<br>50 | Val | Pro | Asp | Glu<br>55 | Asp | Gly |  |

| GAG | GGG | GTC | GCC | ACC | CCG | GCG | CCC | GCC | GCC | AAC | GCG | TCG | GTC | GAG | GCC | 305 |
|---|---|---|---|---|---|---|---|---|---|---|---|---|---|---|---|---|
| Glu | Gly | Val<br>60 | Ala | Thr | Pro | Ala<br>65 | Pro | Ala | Ala | Asn | Ala<br>70 | Ser | Val | Glu | Ala |  |

| GGC | CGC | GCG | ACG | CTG | CGG | GAA | GAC | CTG | CGG | GAG | ATC | AAG | GCC | CGG | GAC | 353 |
|---|---|---|---|---|---|---|---|---|---|---|---|---|---|---|---|---|
| Gly | Arg | Ala<br>75 | Thr | Leu | Arg | Glu | Asp<br>80 | Leu | Arg | Glu | Ile | Lys<br>85 | Ala | Arg | Asp |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GGC | GAC | GCG | ACC | TTC | TAC | GTC | TGC | CCG | CCG | CCG | ACC | GGC | GCC | ACG | GTG | 401  |
| Gly | Asp | Ala | Thr | Phe | Tyr | Val | Cys | Pro | Pro | Pro | Thr | Gly | Ala | Thr | Val |      |
| 90  |     |     |     |     | 95  |     |     |     |     | 100 |     |     |     |     | 105 |      |
| GTG | CAG | TTC | GAG | CAG | CCC | CGG | CCG | TGC | CCG | CGC | GCG | CCC | GAC | GGC | CAG | 449  |
| Val | Gln | Phe | Glu | Gln | Pro | Arg | Pro | Cys | Pro | Arg | Ala | Pro | Asp | Gly | Gln |      |
|     |     |     |     | 110 |     |     |     |     | 115 |     |     |     |     | 120 |     |      |
| AAC | TAC | ACG | GAG | GGG | ATC | GCG | GTC | GTC | TTC | AAG | GAG | AAC | ATC | GCC | CCG | 497  |
| Asn | Tyr | Thr | Glu | Gly | Ile | Ala | Val | Val | Phe | Lys | Glu | Asn | Ile | Ala | Pro |      |
|     |     |     | 125 |     |     |     |     | 130 |     |     |     |     | 135 |     |     |      |
| TAC | AAG | TTC | AAG | GCC | ACC | ATG | TAC | TAC | AAG | GAC | GTG | ACC | GTC | TCG | CAG | 545  |
| Tyr | Lys | Phe | Lys | Ala | Thr | Met | Tyr | Tyr | Lys | Asp | Val | Thr | Val | Ser | Gln |      |
|     |     | 140 |     |     |     |     | 145 |     |     |     |     | 150 |     |     |     |      |
| GTC | TGG | TTC | GGG | CAC | CGG | TAC | TCG | CAG | TTC | ATG | GGG | ATC | TTC | GAG | GAC | 593  |
| Val | Trp | Phe | Gly | His | Arg | Tyr | Ser | Gln | Phe | Met | Gly | Ile | Phe | Glu | Asp |      |
|     | 155 |     |     |     |     | 160 |     |     |     |     | 165 |     |     |     |     |      |
| CGC | GCC | CCC | GTG | CCC | TTC | GAG | GAG | GTG | ATG | GAC | AAG | ATC | AAC | GCC | AAG | 641  |
| Arg | Ala | Pro | Val | Pro | Phe | Glu | Glu | Val | Met | Asp | Lys | Ile | Asn | Ala | Lys |      |
| 170 |     |     |     |     | 175 |     |     |     |     | 180 |     |     |     |     | 185 |      |
| GGG | GTC | TGC | CGG | TCG | ACG | GCC | AAG | TAC | GTG | CGG | AAC | AAC | ATG | GAG | AGC | 689  |
| Gly | Val | Cys | Arg | Ser | Thr | Ala | Lys | Tyr | Val | Arg | Asn | Asn | Met | Glu | Ser |      |
|     |     |     |     | 190 |     |     |     |     | 195 |     |     |     |     | 200 |     |      |
| ACG | GCC | TTC | CAC | CGC | GAC | GAC | CAC | GAG | TCG | GAC | ATG | GCG | CTG | AAG | CCG | 737  |
| Thr | Ala | Phe | His | Arg | Asp | Asp | His | Glu | Ser | Asp | Met | Ala | Leu | Lys | Pro |      |
|     |     |     | 205 |     |     |     |     | 210 |     |     |     |     | 215 |     |     |      |
| GCC | AAG | GCC | GCG | ACC | CGC | ACC | AGC | CGC | GGC | TGG | CAC | ACC | ACC | GAC | CTC | 785  |
| Ala | Lys | Ala | Ala | Thr | Arg | Thr | Ser | Arg | Gly | Trp | His | Thr | Thr | Asp | Leu |      |
|     |     | 220 |     |     |     |     | 225 |     |     |     |     | 230 |     |     |     |      |
| AAG | TAC | AAC | CCC | GCG | CGG | GTC | GAG | GCC | TTC | CAC | CGC | TAC | GGC | ACC | ACG | 833  |
| Lys | Tyr | Asn | Pro | Ala | Arg | Val | Glu | Ala | Phe | His | Arg | Tyr | Gly | Thr | Thr |      |
|     | 235 |     |     |     |     | 240 |     |     |     |     | 245 |     |     |     |     |      |
| GTG | AAC | TGT | ATC | GTC | GAG | GAG | GTG | GAG | GCC | CGC | TCG | GTG | TAC | CCG | TAC | 881  |
| Val | Asn | Cys | Ile | Val | Glu | Glu | Val | Glu | Ala | Arg | Ser | Val | Tyr | Pro | Tyr |      |
| 250 |     |     |     |     | 255 |     |     |     |     | 260 |     |     |     |     | 265 |      |
| GAC | GAG | TTC | GTG | CTG | GCG | ACC | GGG | GAC | TTT | GTG | TAC | ATG | TCG | CCG | TTC | 929  |
| Asp | Glu | Phe | Val | Leu | Ala | Thr | Gly | Asp | Phe | Val | Tyr | Met | Ser | Pro | Phe |      |
|     |     |     |     | 270 |     |     |     |     | 275 |     |     |     |     | 280 |     |      |
| TAC | GGC | TAC | CGC | GAC | GGG | TCC | CAC | GGG | GAG | CAC | ACG | GCC | TAC | GCC | GCG | 977  |
| Tyr | Gly | Tyr | Arg | Asp | Gly | Ser | His | Gly | Glu | His | Thr | Ala | Tyr | Ala | Ala |      |
|     |     |     | 285 |     |     |     |     | 290 |     |     |     |     | 295 |     |     |      |
| GAC | CGC | TTC | CGG | CAG | GTC | GAC | GGC | TAC | TAC | GAG | CGC | GAC | CTC | TCG | ACG | 1025 |
| Asp | Arg | Phe | Arg | Gln | Val | Asp | Gly | Tyr | Tyr | Glu | Arg | Asp | Leu | Ser | Thr |      |
|     |     | 300 |     |     |     |     | 305 |     |     |     |     | 310 |     |     |     |      |
| GGC | CGC | CGC | GCC | GCC | GCG | CCG | GTG | ACG | CGC | AAC | CTG | CTG | ACC | ACC | CCC | 1073 |
| Gly | Arg | Arg | Ala | Ala | Ala | Pro | Val | Thr | Arg | Asn | Leu | Leu | Thr | Thr | Pro |      |
|     | 315 |     |     |     |     | 320 |     |     |     |     | 325 |     |     |     |     |      |
| AAG | TTC | ACC | GTG | GGC | TGG | GAC | TGG | GCC | CCC | AAG | CGC | CCC | TCG | GTC | TGC | 1121 |
| Lys | Phe | Thr | Val | Gly | Trp | Asp | Trp | Ala | Pro | Lys | Arg | Pro | Ser | Val | Cys |      |
| 330 |     |     |     |     | 335 |     |     |     |     | 340 |     |     |     |     | 345 |      |
| ACG | CTG | ACC | AAG | TGG | CGG | GAG | GTG | GAC | GAG | ATG | CTG | CGC | GCC | GAG | TAC | 1169 |
| Thr | Leu | Thr | Lys | Trp | Arg | Glu | Val | Asp | Glu | Met | Leu | Arg | Ala | Glu | Tyr |      |
|     |     |     |     | 350 |     |     |     |     | 355 |     |     |     |     | 360 |     |      |
| GGC | CCC | TCG | TTC | CGC | TTC | TCC | TCG | GCC | GCC | CTC | TCG | ACC | ACC | TTC | ACC | 1217 |
| Gly | Pro | Ser | Phe | Arg | Phe | Ser | Ser | Ala | Ala | Leu | Ser | Thr | Thr | Phe | Thr |      |
|     |     |     | 365 |     |     |     |     | 370 |     |     |     |     | 375 |     |     |      |
| GCC | AAC | CGC | ACC | GAG | TAC | GCC | CTG | TCG | CGC | GTC | GAC | CTC | GCG | GAC | TGC | 1265 |
| Ala | Asn | Arg | Thr | Glu | Tyr | Ala | Leu | Ser | Arg | Val | Asp | Leu | Ala | Asp | Cys |      |
|     |     | 380 |     |     |     |     | 385 |     |     |     |     | 390 |     |     |     |      |
| GTC | GGG | CGC | GAG | GCC | CGC | GAG | GCC | GTG | GAC | CGC | ATC | TTC | CTC | CGG | CGC | 1313 |
| Val | Gly | Arg | Glu | Ala | Arg | Glu | Ala | Val | Asp | Arg | Ile | Phe | Leu | Arg | Arg |      |
|     | 395 |     |     |     |     | 400 |     |     |     |     | 405 |     |     |     |     |      |

```
TAC AAC GGG ACG CAC GTG AAG GTG GGC CAG GTG CAG TAC TAC CTG GCC        1361
Tyr Asn Gly Thr His Val Lys Val Gly Gln Val Gln Tyr Tyr Leu Ala
410             415             420             425

ACG GGC GGC TTC CTC ATC GCG TAC CAG CCC CTC CTC AGC AAC GCG CTC        1409
Thr Gly Gly Phe Leu Ile Ala Tyr Gln Pro Leu Leu Ser Asn Ala Leu
                430             435             440

GTG GAG CTC TAC GTG CGG GAG CTC GTC CGC GAG CAG ACG CGG CGG CCG        1457
Val Glu Leu Tyr Val Arg Glu Leu Val Arg Glu Gln Thr Arg Arg Pro
                445             450             455

GCC GGG GGC GAC CCC GGG GAG GCG GCC ACC CCG GGC CCC TCC GTG GAC        1505
Ala Gly Gly Asp Pro Gly Glu Ala Ala Thr Pro Gly Pro Ser Val Asp
460             465             470

CCC CCC AGC GTG GAG CGC ATC AAG ACC ACG TCC TCG GTC GAG TTC GCG        1553
Pro Pro Ser Val Glu Arg Ile Lys Thr Thr Ser Ser Val Glu Phe Ala
475             480             485

CGC CTG CAG TTC ACG TAC GAC CAC ATC CAG CGC CAC GTC AAC GAC ATG        1601
Arg Leu Gln Phe Thr Tyr Asp His Ile Gln Arg His Val Asn Asp Met
490             495             500             505

CTG GGG CGC ATC GCC ATC GCC TGG TGC GAG CTG CAG AAC CGC GAG CTG        1649
Leu Gly Arg Ile Ala Ile Ala Trp Cys Glu Leu Gln Asn Arg Glu Leu
                510             515             520

ACG CTG TGG AAC GAG GCC CGC CGG CTG AAC CCC GGG GCC ATC GCC TCG        1697
Thr Leu Trp Asn Glu Ala Arg Arg Leu Asn Pro Gly Ala Ile Ala Ser
                525             530             535

GCC ACC GTG GGC CGC CGG GTG AGC GCG CGC ATG CTC GGG GAC GTC ATG        1745
Ala Thr Val Gly Arg Arg Val Ser Ala Arg Met Leu Gly Asp Val Met
            540             545             550

GCC GTC TCG ACC TGC GTG CCC GTG GCC CCC GAC AAC GTC ATC ATG CAG        1793
Ala Val Ser Thr Cys Val Pro Val Ala Pro Asp Asn Val Ile Met Gln
555             560             565

AAC TCG ATG CGC GTG GCC GCG CGC CCC GGG ACG TGC TAC AGC CGC CCC        1841
Asn Ser Met Arg Val Ala Ala Arg Pro Gly Thr Cys Tyr Ser Arg Pro
570             575             580             585

CTG GTC AGC TTC CGC TAC GAG GCC GAC GGG CCC CTC GTC GAG GGC CAG        1889
Leu Val Ser Phe Arg Tyr Glu Ala Asp Gly Pro Leu Val Glu Gly Gln
                590             595             600

CTG GGC GAG GAC AAC GAG ATC CGC CTC GAG CGC GAC GCC CTG GAG CCC        1937
Leu Gly Glu Asp Asn Glu Ile Arg Leu Glu Arg Asp Ala Leu Glu Pro
                605             610             615

TGC ACC GTC GGC CAC CGC CGG TAC TTC ACC TTC GGG GCG GGC TAC GTG        1985
Cys Thr Val Gly His Arg Arg Tyr Phe Thr Phe Gly Ala Gly Tyr Val
        620             625             630

TAC TTT GAG GAG TAC GCC TAC TCC CAT CAG CTG GGC CGC GCC GAC GTG        2033
Tyr Phe Glu Glu Tyr Ala Tyr Ser His Gln Leu Gly Arg Ala Asp Val
    635             640             645

ACG ACC GTT AGC ACG TTC ATC AAC CTC AAC CTC ACG ATG CTC GAG GAC        2081
Thr Thr Val Ser Thr Phe Ile Asn Leu Asn Leu Thr Met Leu Glu Asp
650             655             660             665

CAC GAG TTC GTG CCC CTG GAG GTG TAC ACC CGC CAG GAG ATC AAG GAC        2129
His Glu Phe Val Pro Leu Glu Val Tyr Thr Arg Gln Glu Ile Lys Asp
                670             675             680

AGC GGC CTG CTG GAC TAC ACC GAG GTC CAG CGC CGC AAC CAG CTC CAC        2177
Ser Gly Leu Leu Asp Tyr Thr Glu Val Gln Arg Arg Asn Gln Leu His
                685             690             695

GCG CTC CGC TTC GCC GAC ATC GAC ACG GTC ATC AAG GCC GAC GCA CAC        2225
Ala Leu Arg Phe Ala Asp Ile Asp Thr Val Ile Lys Ala Asp Ala His
            700             705             710

GCC GCC CTC TTC GCG GGC CTC TAC TCC TTC TTC GAG GGC CTC GGG GAC        2273
Ala Ala Leu Phe Ala Gly Leu Tyr Ser Phe Phe Glu Gly Leu Gly Asp
715             720             725
```

| | | | | | | | | | | | | | | | | |
|---|---|---|---|---|---|---|---|---|---|---|---|---|---|---|---|---|
| GTG | GGC | CGC | GCG | GTC | GGA | AAG | GTC | GTC | ATG | GGC | ATC | GTG | GGC | GGG | GTC | 2321 |
| Val | Gly | Arg | Ala | Val | Gly | Lys | Val | Val | Met | Gly | Ile | Val | Gly | Gly | Val | |
| 730 | | | | | 735 | | | | 740 | | | | | | 745 | |
| GTC | TCC | GCC | GTC | TCG | GGC | GTG | TCC | TCG | TTC | CTC | TCC | AAC | CCC | TTC | GGG | 2369 |
| Val | Ser | Ala | Val | Ser | Gly | Val | Ser | Ser | Phe | Leu | Ser | Asn | Pro | Phe | Gly | |
| | | | | 750 | | | | 755 | | | | | 760 | | | |
| GCC | CTG | GCC | GTG | GGG | CTG | CTG | GTC | CTG | GCG | GGG | CTG | GCG | GCC | GCC | TTC | 2417 |
| Ala | Leu | Ala | Val | Gly | Leu | Leu | Val | Leu | Ala | Gly | Leu | Ala | Ala | Ala | Phe | |
| | | | 765 | | | | | 770 | | | | | 775 | | | |
| TTC | GCC | TTC | CGC | TAC | GTC | ATG | CGC | CTG | CAG | CGG | AAC | CCC | ATG | AAG | GCC | 2465 |
| Phe | Ala | Phe | Arg | Tyr | Val | Met | Arg | Leu | Gln | Arg | Asn | Pro | Met | Lys | Ala | |
| | | 780 | | | | | 785 | | | | | 790 | | | | |
| CTG | TAC | CCG | CTG | ACC | ACC | AAG | GAG | CTC | AAG | AGC | GAC | GGC | GCG | CCG | CTG | 2513 |
| Leu | Tyr | Pro | Leu | Thr | Thr | Lys | Glu | Leu | Lys | Ser | Asp | Gly | Ala | Pro | Leu | |
| | 795 | | | | | 800 | | | | | 805 | | | | | |
| GCG | GGC | GGC | GGC | GAG | GAC | GGC | GCG | GAG | GAC | TTT | GAC | GAG | GCC | AAG | CTG | 2561 |
| Ala | Gly | Gly | Gly | Glu | Asp | Gly | Ala | Glu | Asp | Phe | Asp | Glu | Ala | Lys | Leu | |
| 810 | | | | | 815 | | | | | 820 | | | | | 825 | |
| GCG | CAG | GCG | CGG | GAG | ATG | ATC | CGC | TAC | ATG | GCC | CTG | GTC | TCG | GCC | ATG | 2609 |
| Ala | Gln | Ala | Arg | Glu | Met | Ile | Arg | Tyr | Met | Ala | Leu | Val | Ser | Ala | Met | |
| | | | | 830 | | | | | 835 | | | | | 840 | | |
| GAG | CGC | ACC | GAG | CAC | AAG | GCC | CGC | AAG | AAG | GGC | ACG | AGC | GCC | CTG | CTG | 2657 |
| Glu | Arg | Thr | Glu | His | Lys | Ala | Arg | Lys | Lys | Gly | Thr | Ser | Ala | Leu | Leu | |
| | | | 845 | | | | | 850 | | | | | 855 | | | |
| AGC | GCG | AAG | GTT | ACC | GAC | GCG | GTG | ATG | CGA | AAG | CGC | GCC | CGG | CCC | CGG | 2705 |
| Ser | Ala | Lys | Val | Thr | Asp | Ala | Val | Met | Arg | Lys | Arg | Ala | Arg | Pro | Arg | |
| | | 860 | | | | | 865 | | | | | 870 | | | | |
| TAC | TCT | CCC | CTC | CGC | GAC | ACG | GAC | GAG | GAG | GAA | CTG | TAGCGGCCCG | | | | 2751 |
| Tyr | Ser | Pro | Leu | Arg | Asp | Thr | Asp | Glu | Glu | Glu | Leu | | | | | |
| | 875 | | | | | 880 | | | | | 885 | | | | | |

```
AGCGGACCCG ACCCCGACCC CAGAGAATGC TCAATAAACT ATGACAAAAA ACACACGCGG      2811

TGTGATCGGT GACGGATCGT TTGTGCGTCG GAAGCGCGCG GGCGGCTTCG GTCCCACGGG      2871

GCTACCCCGC CCGGGGGGGA TCTGGTAGGG CAGACCCCAT CCCACCCCCT CCCCCGGGGG      2931

AGGGGGACAG AA                                                          2943
```

( 2 ) INFORMATION FOR SEQ ID NO:8:

( i ) SEQUENCE CHARACTERISTICS:
        ( A ) LENGTH: 885 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Arg | Pro | Arg | Gly | Thr | Pro | Pro | Ser | Phe | Leu | Pro | Leu | Pro | Val | Leu |
| 1 | | | | 5 | | | | | 10 | | | | | 15 | |
| Leu | Ala | Leu | Ala | Val | Ile | Ala | Ala | Ala | Gly | Arg | Ala | Ala | Pro | Ala | Ala |
| | | | 20 | | | | | 25 | | | | | 30 | | |
| Ala | Ala | Ala | Pro | Thr | Ala | Asp | Pro | Ala | Ala | Thr | Pro | Ala | Leu | Pro | Glu |
| | | 35 | | | | | 40 | | | | | 45 | | | |
| Asp | Glu | Glu | Val | Pro | Asp | Glu | Asp | Gly | Glu | Gly | Val | Ala | Thr | Pro | Ala |
| | 50 | | | | | 55 | | | | | 60 | | | | |
| Pro | Ala | Ala | Asn | Ala | Ser | Val | Glu | Ala | Gly | Arg | Ala | Thr | Leu | Arg | Glu |
| 65 | | | | | 70 | | | | | 75 | | | | | 80 |
| Asp | Leu | Arg | Glu | Ile | Lys | Ala | Arg | Asp | Gly | Asp | Ala | Thr | Phe | Tyr | Val |
| | | | | 85 | | | | | 90 | | | | | 95 | |
| Cys | Pro | Pro | Pro | Thr | Gly | Ala | Thr | Val | Val | Gln | Phe | Glu | Gln | Pro | Arg |

-continued

```
                    100                           105                           110
    Pro  Cys  Pro  Arg  Ala  Pro  Asp  Gly  Gln  Asn  Tyr  Thr  Glu  Gly  Ile  Ala
              115                      120                      125

Val  Val  Phe  Lys  Glu  Asn  Ile  Ala  Pro  Tyr  Lys  Phe  Lys  Ala  Thr  Met
         130                      135                      140

Tyr  Tyr  Lys  Asp  Val  Thr  Val  Ser  Gln  Val  Trp  Phe  Gly  His  Arg  Tyr
    145                      150                      155                      160

Ser  Gln  Phe  Met  Gly  Ile  Phe  Glu  Asp  Arg  Ala  Pro  Val  Pro  Phe  Glu
                   165                      170                      175

Glu  Val  Met  Asp  Lys  Ile  Asn  Ala  Lys  Gly  Val  Cys  Arg  Ser  Thr  Ala
                   180                      185                      190

Lys  Tyr  Val  Arg  Asn  Asn  Met  Glu  Ser  Thr  Ala  Phe  His  Arg  Asp  Asp
              195                      200                      205

His  Glu  Ser  Asp  Met  Ala  Leu  Lys  Pro  Ala  Lys  Ala  Ala  Thr  Arg  Thr
         210                      215                      220

Ser  Arg  Gly  Trp  His  Thr  Thr  Asp  Leu  Lys  Tyr  Asn  Pro  Ala  Arg  Val
    225                      230                      235                      240

Glu  Ala  Phe  His  Arg  Tyr  Gly  Thr  Thr  Val  Asn  Cys  Ile  Val  Glu  Glu
                        245                      250                      255

Val  Glu  Ala  Arg  Ser  Val  Tyr  Pro  Tyr  Asp  Glu  Phe  Val  Leu  Ala  Thr
                   260                      265                      270

Gly  Asp  Phe  Val  Tyr  Met  Ser  Pro  Phe  Tyr  Gly  Tyr  Arg  Asp  Gly  Ser
              275                      280                      285

His  Gly  Glu  His  Thr  Ala  Tyr  Ala  Ala  Asp  Arg  Phe  Arg  Gln  Val  Asp
         290                      295                      300

Gly  Tyr  Tyr  Glu  Arg  Asp  Leu  Ser  Thr  Gly  Arg  Arg  Ala  Ala  Ala  Pro
    305                      310                      315                      320

Val  Thr  Arg  Asn  Leu  Leu  Thr  Thr  Pro  Lys  Phe  Thr  Val  Gly  Trp  Asp
                        325                      330                      335

Trp  Ala  Pro  Lys  Arg  Pro  Ser  Val  Cys  Thr  Leu  Thr  Lys  Trp  Arg  Glu
                   340                      345                      350

Val  Asp  Glu  Met  Leu  Arg  Ala  Glu  Tyr  Gly  Pro  Ser  Phe  Arg  Phe  Ser
              355                      360                      365

Ser  Ala  Ala  Leu  Ser  Thr  Thr  Phe  Thr  Ala  Asn  Arg  Thr  Glu  Tyr  Ala
         370                      375                      380

Leu  Ser  Arg  Val  Asp  Leu  Ala  Asp  Cys  Val  Gly  Arg  Glu  Ala  Arg  Glu
    385                      390                      395                      400

Ala  Val  Asp  Arg  Ile  Phe  Leu  Arg  Arg  Tyr  Asn  Gly  Thr  His  Val  Lys
                        405                      410                      415

Val  Gly  Gln  Val  Gln  Tyr  Tyr  Leu  Ala  Thr  Gly  Gly  Phe  Leu  Ile  Ala
                   420                      425                      430

Tyr  Gln  Pro  Leu  Leu  Ser  Asn  Ala  Leu  Val  Glu  Leu  Tyr  Val  Arg  Glu
              435                      440                      445

Leu  Val  Arg  Glu  Gln  Thr  Arg  Arg  Pro  Ala  Gly  Gly  Asp  Pro  Gly  Glu
         450                      455                      460

Ala  Ala  Thr  Pro  Gly  Pro  Ser  Val  Asp  Pro  Pro  Ser  Val  Glu  Arg  Ile
    465                      470                      475                      480

Lys  Thr  Thr  Ser  Ser  Val  Glu  Phe  Ala  Arg  Leu  Gln  Phe  Thr  Tyr  Asp
                        485                      490                      495

His  Ile  Gln  Arg  His  Val  Asn  Asp  Met  Leu  Gly  Arg  Ile  Ala  Ile  Ala
                   500                      505                      510

Trp  Cys  Glu  Leu  Gln  Asn  Arg  Glu  Leu  Thr  Leu  Trp  Asn  Glu  Ala  Arg
              515                      520                      525
```

```
Arg  Leu  Asn  Pro  Gly  Ala  Ile  Ala  Ser  Ala  Thr  Val  Gly  Arg  Arg  Val
     530                520                          540

Ser  Ala  Arg  Met  Leu  Gly  Asp  Val  Met  Ala  Val  Ser  Thr  Cys  Val  Pro
545                      550                     555                          560

Val  Ala  Pro  Asp  Asn  Val  Ile  Met  Gln  Asn  Ser  Met  Arg  Val  Ala  Ala
                    565                     570                          575

Arg  Pro  Gly  Thr  Cys  Tyr  Ser  Arg  Pro  Leu  Val  Ser  Phe  Arg  Tyr  Glu
               580                     585                          590

Ala  Asp  Gly  Pro  Leu  Val  Glu  Gly  Gln  Leu  Gly  Glu  Asp  Asn  Glu  Ile
               595                     600                     605

Arg  Leu  Glu  Arg  Asp  Ala  Leu  Glu  Pro  Cys  Thr  Val  Gly  His  Arg  Arg
     610                     615                          620

Tyr  Phe  Thr  Phe  Gly  Ala  Gly  Tyr  Val  Tyr  Phe  Glu  Glu  Tyr  Ala  Tyr
625                      630                     635                          640

Ser  His  Gln  Leu  Gly  Arg  Ala  Asp  Val  Thr  Thr  Val  Ser  Thr  Phe  Ile
                    645                     650                          655

Asn  Leu  Asn  Leu  Thr  Met  Leu  Glu  Asp  His  Glu  Phe  Val  Pro  Leu  Glu
               660                     665                          670

Val  Tyr  Thr  Arg  Gln  Glu  Ile  Lys  Asp  Ser  Gly  Leu  Leu  Asp  Tyr  Thr
          675                          680                          685

Glu  Val  Gln  Arg  Arg  Asn  Gln  Leu  His  Ala  Leu  Arg  Phe  Ala  Asp  Ile
     690                          695                     700

Asp  Thr  Val  Ile  Lys  Ala  Asp  Ala  His  Ala  Ala  Leu  Phe  Ala  Gly  Leu
705                     710                          715                          720

Tyr  Ser  Phe  Phe  Glu  Gly  Leu  Gly  Asp  Val  Gly  Arg  Ala  Val  Gly  Lys
                    725                          730                          735

Val  Val  Met  Gly  Ile  Val  Gly  Gly  Val  Val  Ser  Ala  Val  Ser  Gly  Val
               740                          745                     750

Ser  Ser  Phe  Leu  Ser  Asn  Pro  Phe  Gly  Ala  Leu  Ala  Val  Gly  Leu  Leu
          755                     760                          765

Val  Leu  Ala  Gly  Leu  Ala  Ala  Ala  Phe  Phe  Ala  Phe  Arg  Tyr  Val  Met
     770                     775                          780

Arg  Leu  Gln  Arg  Asn  Pro  Met  Lys  Ala  Leu  Tyr  Pro  Leu  Thr  Thr  Lys
785                     790                          795                          800

Glu  Leu  Lys  Ser  Asp  Gly  Ala  Pro  Leu  Ala  Gly  Gly  Gly  Glu  Asp  Gly
               805                          810                          815

Ala  Glu  Asp  Phe  Asp  Glu  Ala  Lys  Leu  Ala  Gln  Ala  Arg  Glu  Met  Ile
               820                     825                          830

Arg  Tyr  Met  Ala  Leu  Val  Ser  Ala  Met  Glu  Arg  Thr  Glu  His  Lys  Ala
          835                     840                     845

Arg  Lys  Lys  Gly  Thr  Ser  Ala  Leu  Leu  Ser  Ala  Lys  Val  Thr  Asp  Ala
     850                     855                     860

Val  Met  Arg  Lys  Arg  Ala  Arg  Pro  Arg  Tyr  Ser  Pro  Leu  Arg  Asp  Thr
865                     870                          875                          880

Asp  Glu  Glu  Glu  Leu
               885
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:9:

TTCACCGTGG CCTGGGACTG G                                         21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:10:

GCGATTCTGC AGCTCGCACC A                                         21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:11:

TTCACCGTGG GCTGGGACTG G                                         21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:12:

GCGGTTCTGG AGCTCGCACC A                                         21